(12) United States Patent
Seul et al.

(10) Patent No.: US 6,387,707 B1
(45) Date of Patent: *May 14, 2002

(54) ARRAY CYTOMETRY

(75) Inventors: Michael Seul, Fanwood; Alice Xiang Li, Piscataway, both of NJ (US)

(73) Assignee: Bioarray Solutions, Piscataway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/320,274

(22) Filed: May 28, 1999

Related U.S. Application Data

(63) Continuation-in-part of application No. 09/171,550, filed as application No. PCT/US97/08159 on Apr. 24, 1997, now Pat. No. 6,251,691.
(60) Provisional application No. 60/016,642, filed on Apr. 25, 1996.

(51) Int. Cl.$^7$ .................. G01N 25/20; G01N 21/20
(52) U.S. Cl. .................. 436/164; 422/57; 422/60; 422/63; 422/67; 422/68.1; 422/50; 435/4; 435/6; 435/7.1; 435/7.2; 435/7.21; 435/7.23; 435/7.92; 435/7.93; 435/7.94; 435/7.95; 427/2.12; 427/2.13; 427/483; 427/59; 427/77; 436/519; 436/538; 436/806; 436/807
(58) Field of Search .................. 435/4, 6, 7.1, 7.2, 435/7.21, 7.23, 7.92, 7.93–7.95; 422/50, 57, 60, 63, 67, 68.1; 427/2.12, 2.13, 483, 59, 77; 436/519, 538, 806, 807

(56) References Cited

U.S. PATENT DOCUMENTS

| | | | |
|---|---|---|---|
| 3,982,182 A | 9/1976 | Hogg | 324/71 |
| 3,998,525 A | 12/1976 | Giglia | 350/160 |

(List continued on next page.)

FOREIGN PATENT DOCUMENTS

| | | | |
|---|---|---|---|
| WO | 9512808 | 5/1995 | G01N/21/00 |
| WO | 9604547 | 2/1996 | G01N/27/00 |

(List continued on next page.)

OTHER PUBLICATIONS

Micheletto et al., *Iangmuir*, vol. 11, 3333–3336 (1995).
Nagayama et al., *Phase Transitions*, vol. 45, 185–203 (1993).
Yeh, et al., "Assembly of ordered colloidal aggregates by electric–field–induced fluid flow," *Nature*, vol. 386.6: 57–59 (1997).

(List continued on next page.)

*Primary Examiner*—Long V. Le
*Assistant Examiner*—Pensee T. Do
(74) *Attorney, Agent, or Firm*—Julie Bowker

(57) ABSTRACT

A method and apparatus for the manipulation of colloidal particulates and biomolecules at the interface between an insulating electrode such as silicon oxide and an electrolyte solution. Light-controlled electrokinetic assembly of particles near surfaces relies on the combination of three functional elements: the AC electric field-induced assembly of planar aggregates; the patterning of the electrolyte/silicon oxide/silicon interface to exert spatial control over the assembly process; and the real-time control of the assembly process via external illumination. The present invention provides a set of fundamental operations enabling interactive control over the creation and placement of planar arrays of several types of particles and biomolecules and the manipulation of array shape and size. The present invention enables sample preparation and handling for diagnostic assays and biochemical analysis in an array format, and the functional integration of these operations. In addition, the present invention provides a procedure for the creation of material surfaces with desired properties and for the fabrication of surface-mounted optical components. This invention is also for a method and apparatus to direct the lateral motion and induce the assembly into planar arrays of cells on semiconductor surfaces in response to temporally and spatially varying electric fields and to projected patterns of illumination.

32 Claims, 20 Drawing Sheets

U.S. PATENT DOCUMENTS

| | | | | |
|---|---|---|---|---|
| 4,055,799 A | * | 10/1977 | Coster et al. | 324/71 |
| 4,075,013 A | | 2/1978 | Ward et al. | 96/1.5 |
| 4,456,513 A | | 6/1984 | Kawai et al. | 204/180 |
| 4,575,407 A | | 3/1986 | Diller | 204/67 |
| 4,591,550 A | | 5/1986 | Hafeman et al. | 435/4 |
| 4,717,655 A | | 1/1988 | Fulwyler | 435/7 |
| 4,832,814 A | | 5/1989 | Root | 204/299 |
| 5,444,330 A | | 8/1995 | Leventis et al. | 313/506 |
| 5,447,440 A | | 9/1995 | Davis et al. | 435/6 |
| 5,498,392 A | | 3/1996 | Wilding et al. | 422/68.1 |
| 5,573,909 A | | 11/1996 | Singer et al. | 435/6 |
| 5,585,069 A | | 12/1996 | Zanzucchi et al. | 422/100 |
| 5,587,128 A | | 12/1996 | Wilding et al. | 422/50 |
| 5,593,838 A | | 1/1997 | Zanzucchi et al. | 435/6 |
| 5,723,218 A | | 3/1998 | Haugland et al. | 428/402 |
| 5,744,305 A | | 4/1998 | Fodor et al. | 435/6 |
| 5,807,755 A | | 9/1998 | Ekins | 436/518 |
| 5,837,551 A | | 11/1998 | Ekins | 436/518 |
| 5,855,753 A | | 1/1999 | Trau et al. | 204/484 |
| 5,858,804 A | | 1/1999 | Zanzucchi et al. | 436/536 |
| 5,874,219 A | | 2/1999 | Rava et al. | 435/6 |
| 5,942,388 A | * | 8/1999 | Willner et al. | 435/6 |
| 5,989,835 A | | 11/1999 | Dunlay et al. | 435/7.2 |
| 6,007,996 A | * | 12/1999 | McNamara et al. | 435/6 |
| 6,017,696 A | | 1/2000 | Heller | 435/6 |
| 6,023,540 A | | 2/2000 | Walt et al. | 385/12 |
| 6,033,547 A | | 3/2000 | Trau et al. | 204/622 |
| 6,083,763 A | | 7/2000 | Balch | 436/518 |
| 6,136,468 A | * | 10/2000 | Mitchell, Jr. et al. | 429/110 |
| 6,266,459 B1 | | 7/2001 | Walt et al. | 385/12 |

FOREIGN PATENT DOCUMENTS

| | | | |
|---|---|---|---|
| WO | 9607917 | 3/1996 | G01N/35/00 |
| WO | 9740383 | 10/1997 | G01N/33/543 |
| WO | 9806007 | 2/1998 | G03F/7/00 |
| WO | 9853300 | 11/1998 | G01N/21/00 |
| WO | 9918434 | 4/1999 | G01N/33/50 |
| WO | 9919515 | 4/1999 | C12Q/1/68 |

OTHER PUBLICATIONS

Giersig et al., "Formation of ordered two–dimensional gold colloid lattices by electrophoretic deposition," *J. Phys. Chem.*, vol. 97: 6334–6336.

Seul et al., "Scale transformation of magnetic bubble arrays: coupling of topological disorder and polydispersity," *Science*, vol. 262:558–560 (1993).

Trau et al., "Fiedld–Induced Layering of Colloidal Crystals," *Science*, vol. 272:706–709 (1996).

Seul et al., "Domain Shapes and Patterns: The Phenomenology of modulated Phases," *Science*, vol. 267:476–483 (1995).

Schena et al. "Quantitative Monitoring of Gene Expression Patterns with a Complementary DNA Microarray," *Science*, vol. 270:467–470 (1995).

Haab et al. "Single Molecule Fluorescence Burst Detection of DNA Fragments Separated by Capillary Electrophoresis," *Analytical Chemistry* vol. 67 (No. 18):3253–3256 (1995).

Richetti, et al., *J. Physique Lettr.*, vol. 45:L–1137 to L–1143 (1984).

Sze, "MIS Diode and Charge–Coupled Device," *The Physics of Semiconductors*, Chapter 7, pp. 362–430 ($2^{nd}$ Edition) (Wiley Interscience 1981).

* cited by examiner

22

FIG. 3a
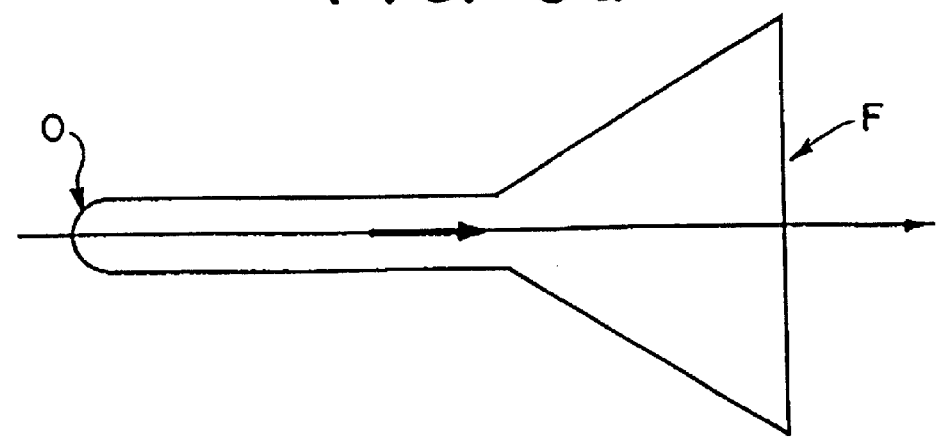
FIG. 3b
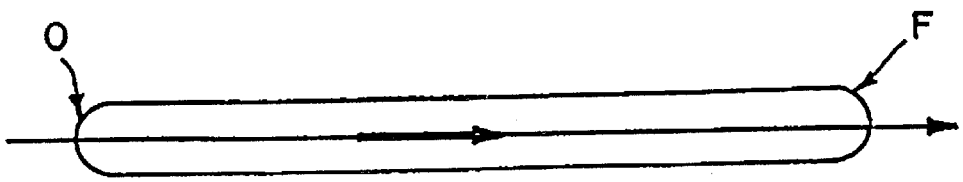

FIG. 5
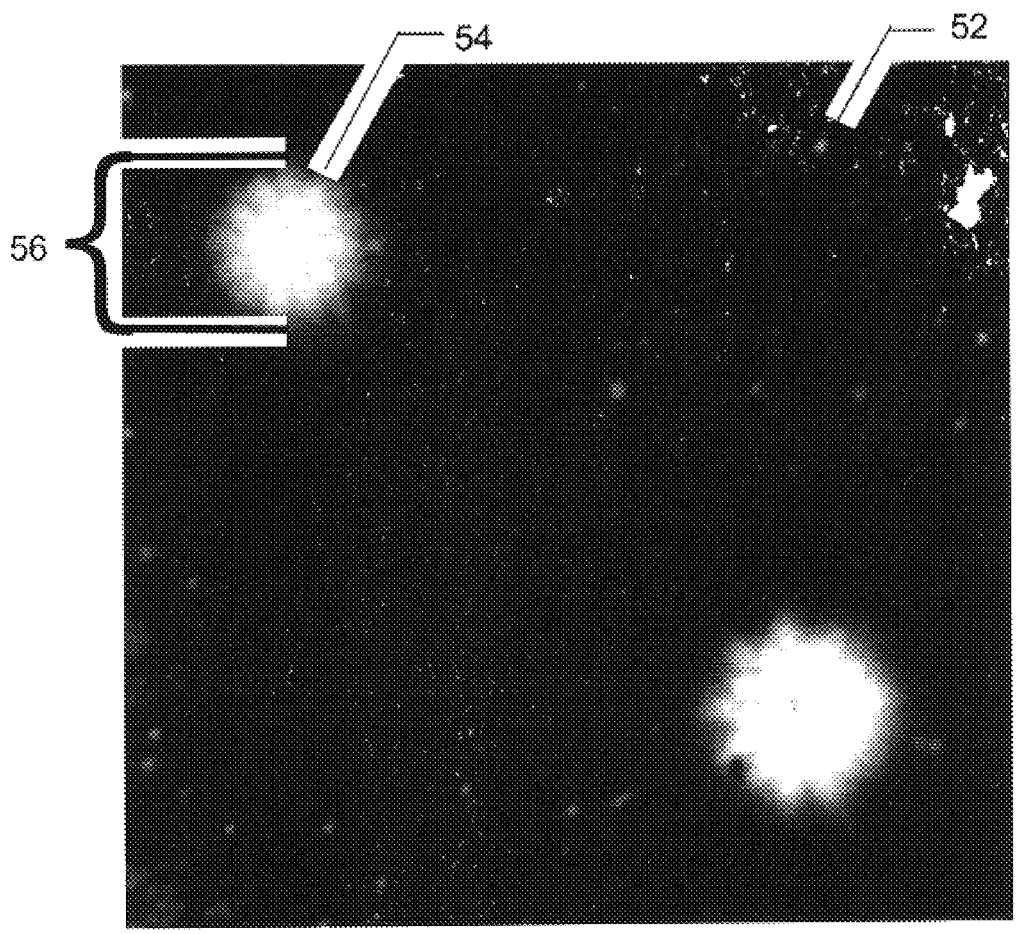
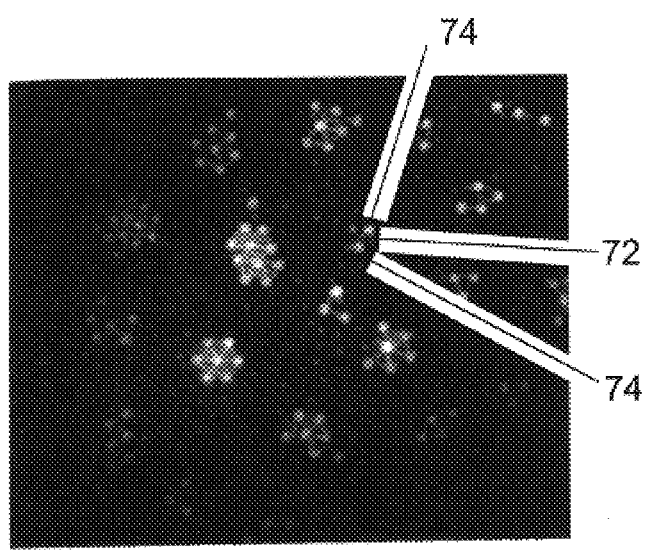
FIG. 7

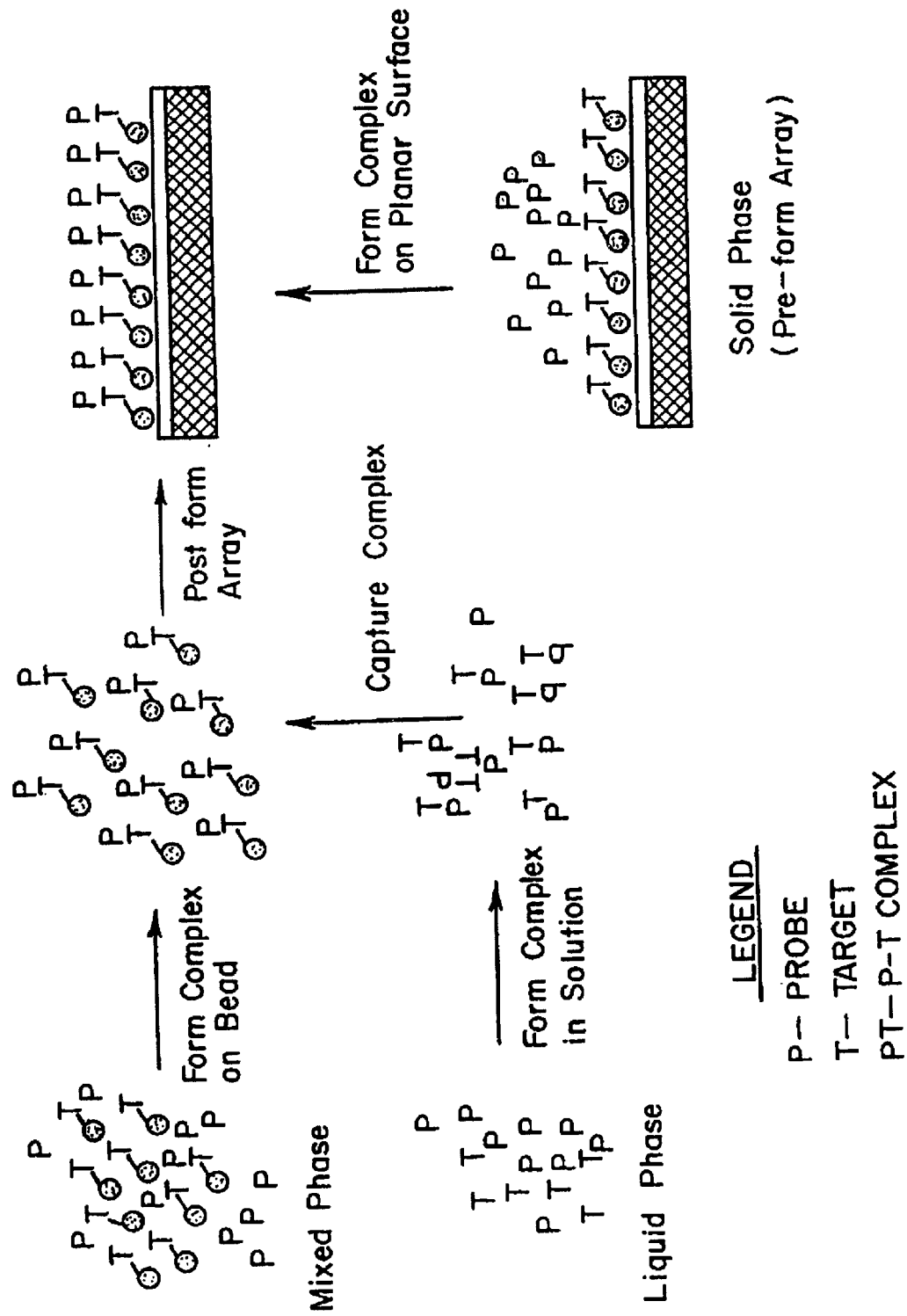

Illuminated Zone

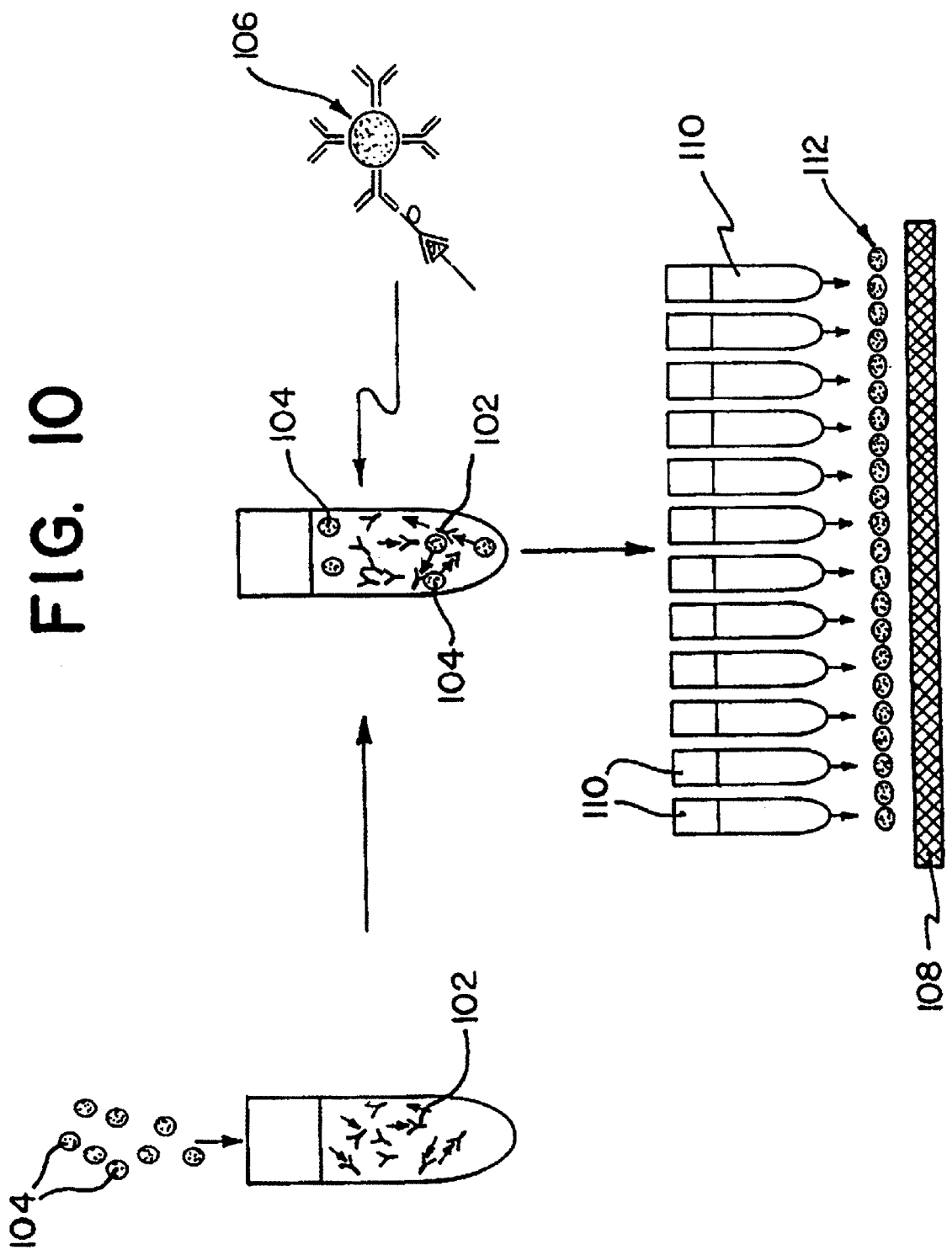

FIG. IIa
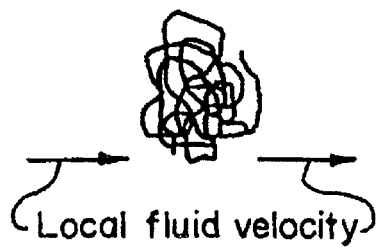
Local fluid velocity
FIG. IIb
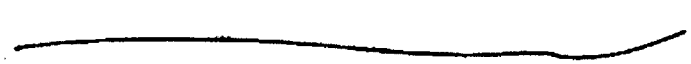
FIG. IIc
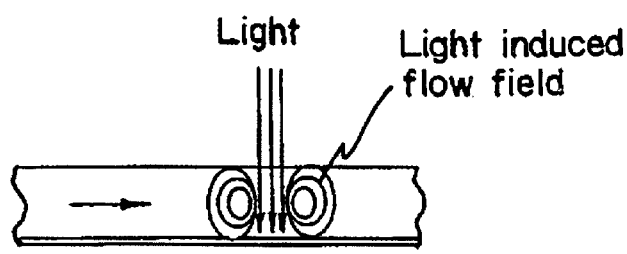
Light  Light induced flow field
FIG. IId
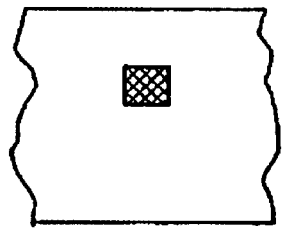
FIG. IIe
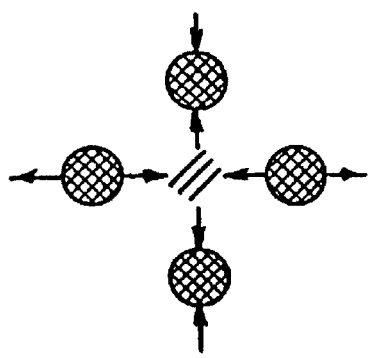

ARRAY CYTOMETRY

This application is a continuation-in-part application of application Ser. No. 09/171,550, filed on Oct. 26, 1998, now U.S. Pat. No. 6,251,691, corresponding to PCT International Application No. PCT/US97/08159, filed on Apr. 24, 1997, which in turn is based on U.S. Provisional Application Serial No. 60/016,642, filed on Apr. 25, 1996. Applicants hereby claim the priority of these prior applications pursuant to 35 U.S.C. §§119 and 120. These prior plications are incorporated herein by reference.

FIELD OF THE INVENTION

The present invention generally relates to the field of materials science and analytical chemistry.

The present invention specifically relates to the realization of a complete, functionally integrated system for the implementation of biochemical analysis in a planar, miniaturized format on the surface of a conductive and/or photoconductive substrate, with applications in pharmaceutical and agricultural drug discovery and in in-vitro or genomic diagnostics. In addition, the method and apparatus of the present invention may be used to create material surfaces exhibiting desirable topographical relief and chemical functionality, and to fabricate surface-mounted optical elements such as lens arrays.

BACKGROUND OF THE INVENTION

I—Ions, Electric Fields and Fluid Flow: Field-induced Formation of Planar Bead Arrays Electrokinesis refers to a class of phenomena elicited by the action of an electric field on the mobile ions surrounding charged objects in an electrolyte solution. When an object of given surface charge is immersed in a solution containing ions, a diffuse ion cloud forms to screen the object's surface charge. This arrangement of a layer of (immobile) charges associated with an immersed object and the screening cloud of (mobile) counter-ions in solution is referred to as a "double layer". In this region of small but finite thickness, the fluid is not electroneutral. Consequently, electric fields acting on this region will set in motion ions in the diffuse layer, and these will in turn entrain the surrounding fluid. The resulting flow fields reflect the spatial distribution of ionic current in the fluid. Electroosmosis represents the simplest example of an electrokinetic phenomenon. It arises when an electric field is applied parallel to the surface of a sample container or electrode exhibiting fixed surface charges, as in the case of a silicon oxide electrode (in the range of neutral pH). As counter-ions in the electrode double layer are accelerated by the electric field, they drag along solvent molecules and set up bulk fluid flow. This effect can be very substantial in narrow capillaries and may be used to advantage to devise fluid pumping systems.

Electrophoresis is a related phenomenon which refers to the field-induced transport of charged particles immersed in an electrolyte. As with electroosmosis, an electric field accelerates mobile ions in the double layer of the particle. If, in contrast to the earlier case, the particle itself is mobile, it will compensate for this field-induced motion of ions (and the resulting ionic current) by moving in the opposite direction. Electrophoresis plays an important role in industrial coating processes and, along with electroosmosis, it is of particular interest in connection with the development of capillary electrophoresis into a mainstay of modem bioanalytical separation technology.

In confined geometries, such as that of a shallow experimental chamber in the form of a "sandwich" of two planar electrodes, the surface charge distribution and topography of the bounding electrode surfaces play a particularly important role in determining the nature and spatial structure of electroosmotic flow. Such a "sandwich" electrochemical cell may be formed by a pair of electrodes separated by a shallow gap. Typically, the bottom electrode will be formed by an oxide-capped silicon wafer, while the other electrode is formed by optically transparent, conducting indium tin oxide (ITO). The silicon (Si) wafer represents a thin slice of a single crystal of silicon which is doped to attain suitable levels of electrical conductivity and insulated from the electrolyte solution by a thin layer of silicon oxide (SiOx).

The reversible aggregation of beads into planar aggregates adjacent to an electrode surface may be induced by a (DC or AC) electric field that is applied normal to the electrode surface. While the phenomenon has been previously observed in a cell formed by a pair of conductive ITO electrodes (Richetti, Prost and Barois, J. Physique Lettr. 45, L-1137 through L-1143 (1984)), the contents of which are incorporated herein by reference, it has been only recently demonstrated that the underlying attractive interaction between beads is mediated by electrokinetic flow (Yeh, Seul and Shraiman, "Assembly of Ordered Colloidal Aggregates by Electric Field Induced Fluid Flow", Nature 386, 57–59 (1997), the contents of which are incorporated herein by reference). This flow reflects the action of lateral non-uniformities in the spatial distribution of the current in the vicinity of the electrode. In the simplest case, such non-uniformities are introduced by the very presence of a colloidal bead near the electrode as a result of the fact that each bead interferes with the motion of ions in the electrolyte. Thus, it has been observed that an individual bead, when placed near the electrode surface, generates a toroidal flow of fluid centered on the bead. Spatial non-uniformities in the properties of the electrode can also be introduced deliberately by several methods to produce lateral fluid flow toward regions of low impedance. These methods are described in subsequent sections below.

Particles embedded in the electrokinetic flow are advected regardless of their specific chemical or biological nature, while simultaneously altering the flow field. As a result, the electric field-induced assembly of planar aggregates and arrays applies to diverse colloidal particles including: beaded polymer resins ("beads"), lipid vesicles, whole chromosomes, cells and biomolecules including proteins and DNA, as well as metal or semiconductor colloids and clusters.

Important for the applications to be described is the fact that the flow-mediated attractive interaction between beads extends to distances far exceeding the characteristic bead dimension. Planar aggregates are formed in response to an externally applied electric field and disassemble when the field is removed. The strength of the applied field determines the strength of the attractive interaction that underlies the array assembly process and thereby selects the specific arrangement adopted by the beads within the array. That is, as a function of increasing applied voltage, beads first form planar aggregates in which particles are mobile and loosely packed, then assume a tighter packing, and finally exhibit a spatial arrangement in the form of a crystalline, or ordered, array resembling a raft of bubbles. The sequence of transitions between states of increasing internal order is reversible, including complete disassembly of planar aggregates when the applied voltage is removed. In another arrangement, at low initial concentration, beads form small clusters which in turn assume positions within an ordered "superstructure".

II—Patterning of Silicon Oxide Electrode Surfaces

Electrode patterning in accordance with a predetermined design facilitates the quasi-permanent modification of the electrical impedance of the EIS (Electrolyte-Insulator Semiconductor) structure of interest here. By spatially modulating the EIS impedance, electrode-patterning determines the ionic current in the vicinity of the electrode. Depending on the frequency of the applied electric field, beads either seek out, or avoid, regions of high ionic current. Spatial patterning therefore conveys explicit external control over the placement and shape of bead arrays.

While patterning may be achieved in many ways, two procedures offer particular advantages. First, UV-mediated re-growth of a thin oxide layer on a properly prepared silicon surface is a convenient methodology that avoids photolithographic resist patterning and etching. In the presence of oxygen, UV illumination mediates the conversion of exposed silicon into oxide. Specifically, the thickness of the oxide layer depends on the exposure time and may thus be spatially modulated by placing patterned masks into the UV illumination path. This modulation in thickness, with typical variations of approximately 10 Angstroms, translates into spatial modulations in the impedance of the Si/SiOx interface while leaving a flat and chemically homogeneous top surface exposed to the electrolyte solution. Second, spatial modulations in the distribution of the electrode surface charge may be produced by UV-mediated photochemical oxidation of a suitable chemical species that is first deposited as a monolayer film on the SiOx surface. This method permits fine control over local features of the electrode double layer and thus over the electrokinetic flow.

A variation of this photochemical modulation is the creation of lateral gradients in the EIS impedance and hence in the current generated in response to the applied electric field. For example, this is readily accomplished by controlling the UV exposure so as to introduce a slow lateral variation in the oxide thickness or in the surface charge density. As discussed below, control over lateral gradients serves to induce lateral bead transport and facilitates the implementation of such fundamental operations as capturing and channeling of beads to a predetermined destination along conduits in the form of impedance features embedded in the Si/SiOx interface. Photochemical patterning of functionalized chemical overlayers also applies to other types of electrode surfaces including ITO.

III—Light-controlled Modulation of the Interfacial Impedance

The spatial and temporal modulation of the EIS-impedance in accordance with a pattern of external illumination provides the basis to control the electrokinetic forces that mediate bead aggregation. The light-modulated electrokinetic assembly of planar colloidal arrays facilitates remote interactive control over the formation, placement and rearrangement of bead arrays in response to corresponding illumination patterns and thereby offers a wide range of interactive manipulations of colloidal beads and biomolecules.

To understand the principle of this methodology, it will be helpful to briefly review pertinent photoelectric properties of semiconductors, or more specifically, those of the EIS structure formed by the Electrolyte solution (E), the Insulating SiOx layer (I) and the Semiconductor (S). The photoelectric characteristics of this structure are closely related to those of a standard Metal-Insulator-Semiconductor (MIS) or Metal-Oxide-Semiconductor (MOS) devices which are described in S. M. Sze, "The Physics of Semiconductors", 2nd Edition, Chapt. 7 (Wiley Interscience 1981), the contents of which are incorporated herein by reference.

The interface between the semiconductor and the insulating oxide layer deserves special attention. Crucial to the understanding of the electrical response of the MOS structure to light is the concept of a space charge region of small but finite thickness that forms at the Si/SiOx interface in the presence of a bias potential. In the case of the EIS structure, an effective bias, in the form of a junction potential, is present under all but very special conditions. The space charge region forms in response to the distortion of the semiconductor's valence and conduction bands ("band bending") in the vicinity of the interface. This condition in turn reflects the fact that, while there is a bias potential across the interface, there is ideally no charge transfer in the presence of the insulating oxide. That is, in electrochemical language, the EIS structure eliminates Faradaic effects. Instead, charges of opposite sign accumulate on either side of the insulating oxide layer and generate a finite polarization.

In the presence of a reverse bias, the valence and conduction band edges of an n-doped semiconductor bend upward near the Si/SiOx interface and electrons flow out of the interfacial region in response to the corresponding potential gradient. As a result, a majority carrier depletion layer is formed in the vicinity of the Si/SiOx interface. Light absorption in the semiconductor provides a mechanism to create electron-hole pairs within this region. Provided that they do not instantaneously recombine, electron-hole pairs are split by the locally acting electric field, and a corresponding photocurrent flows. It is this latter effect that affords control over the electrokinetic assembly of beads in the electrolyte solution.

To understand in more detail the pertinent frequency dependence of the light-induced modulation of the EIS impedance, two aspects of the equivalent circuit representing the EIS structure are noteworthy. First, there are close analogies between the detailed electrical characteristics of the electric double layer at the electrolyte-oxide interface, and the depletion layer at the interface between the semiconductor and the insulator. As with the double layer, the depletion layer exhibits electrical characteristics similar to those of a capacitor with a voltage-dependent capacitance. As discussed, illumination serves to lower the impedance of the depletion layer. Second, given its capacitive electrical response, the oxide layer will pass current only above a characteristic ("threshold") frequency. Consequently, provided that the frequency of the applied voltage exceeds the threshold, illumination can lower the effective impedance of the entire EIS structure.

This effective reduction of the EIS impedance also depends on the light intensity which determines the rate of generation of electron-hole pairs. In the absence of significant recombination, the majority of photogenerated electrons flow out of the depletion region and contribute to the photocurrent. The remaining hole charge accumulates near the Si/SiOx interface and screens the electric field acting in the depletion region. As a result, the rate of recombination increases, and the efficiency of electron-hole separation, and hence the photocurrent, decreases. For given values of frequency and amplitude of the applied voltage, one therefore expects that as the illumination intensity increases, the current initially increases to a maximum level and then decreases. Similarly, the impedance initially decreases to a minimum value (at maximum current) and then decreases.

This intensity dependence may be used to advantage to induce the lateral displacement of beads between fully exposed and partially masked regions of the interface. As the illumination intensity is increased, the fully exposed regions will correspond to the regions of interface of lowest impedance, and hence of highest current, and beads will be drawn into these regions. As the fully exposed regions reach the state of decreasing photocurrent, the effective EIS impedance in those regions may exceed that of partially masked regions, with a resulting inversion of the lateral gradient in current. Beads will then be drawn out of the fully exposed regions. Additionally, time-varying changes in the illumination pattern may be used to effect bead motion.

IV—Integration of Biochemical Analysis in a Miniaturized, Planar Format

The implementation of assays in a planar array format, particularly in the context of biomolecular screening and medical diagnostics, has the advantage of a high degree of parallelity and automation so as to realize high throughput in complex, multi-step analytical protocols. Miniaturization will result in a decrease in pertinent mixing times reflecting the small spatial scale, as well as in a reduction of requisite sample and reagent volumes as well as power requirements. The integration of biochemical analytical techniques into a miniaturized system on the surface of a planar substrate ("chip") would yield substantial improvements in the performance, and reduction in cost, of analytical and diagnostic procedures.

Within the context of DNA manipulation and analysis, initial steps have been taken in this direction (i.e., miniaturization) by combining on a glass substrate, the restriction enzyme treatment of DNA and the subsequent separation of enzyme digests by capillary electrophoresis, see, for example, Ramsey, PCT Publication No. WO 96/04547, the contents of which are incorporated herein by reference, or the amplification of DNA sequences by application of the polymerase chain reaction (PCR) with subsequent electrophoretic separation, see, for example, U.S. Pat. Nos. 5,498,392 and 5,587,128 to Wilding et al., the contents of which are incorporated herein by reference.

While these standard laboratory processes have been demonstrated in a miniaturized format, they have not been used to form a complete system. A complete system will require additional manipulation such as front-end sample processing, binding and functional assays and the detection of small signals followed by information processing. The true challenge is that of complete functional integration because it is here that system architecture and design constraints on individual components will manifest themselves. For example, a fluidic process is required to concatenate analytical steps that require the spatial separation, and subsequent transport to new locations, of sets of analyte. Several possibilities have been considered including electroosmotic pumping and transport of droplets by temperature-induced gradients in local surface tension. While feasible in demonstration experiments, these techniques place rather severe requirements on the overall systems lay-out to handle the very considerable DC voltages required for efficient electroosmotic mixing or to restrict substrate heating when generating thermally generated surface tension gradients so as to avoid adverse effects on protein and other samples.

SUMMARY OF THE INVENTION

The present invention combines three separate functional elements to provide a method and apparatus facilitating the real-time, interactive spatial manipulation of colloidal particles ("beads") and molecules at an interface between a light sensitive electrode and an electrolyte solution. The three functional elements are: the electric field-induced assembly of planar particle arrays at an interface between an insulating or a conductive electrode and an electrolyte solution; the spatial modulation of the interfacial impedance by means of UV-mediated oxide regrowth or surface-chemical patterning; and, finally, the real-time, interactive control over the state of the interfacial impedance by light. The capabilities of the present invention originate in the fact that the spatial distribution of ionic currents, and thus the fluid flow mediating the array assembly, may be adjusted by external intervention. Of particular interest is the introduction of spatial non-uniformities in the properties of the pertinent EIS structure. As described herein, such inhomogeneities, either permanent or temporary in nature, may be produced by taking advantage of the physical and chemical properties of the EIS structure.

The invention relates to the realization of a complete, functionally integrated system for the implementation of biochemical analysis in a planar, miniaturized format on the surface of a silicon wafer or similar substrate. In addition, the method and apparatus of the present invention may be used to create material surfaces exhibiting desirable topographical relief and chemical functionality, and to fabricate surface-mounted optical elements such as lens arrays.

The combination of three functional elements endows the present invention with a set of operational capabilities to manipulate beads and bead arrays in a planar geometry to allow the implementation of biochemical analytical techniques. These fundamental operations apply to aggregates and arrays of colloidal particles including: beaded polymer resins also referred to as latices, vesicles, whole chromosomes, cells and biomolecules including proteins and DNA, as well as metal or semiconductor colloids and clusters.

Sets of colloidal particles may be captured, and arrays may be formed in designated areas on the electrode surface (FIGS. 1a, 1b and FIGS. 2a–d). Particles, and the arrays they form in response to the applied field, may be channeled along conduits of any configuration that are either embedded in the Si/SiOx interface by UV-oxide patterning or delineated by an external pattern of illumination. This channeling (FIGS. 1c, 1d, 1e, FIGS. 3c, 3d), in a direction normal to that of the applied electric field, relies on lateral gradients in the impedance of the EIS structure and hence in the field-induced current. As discussed herein, such gradients may be introduced by appropriate patterns of illumination, and this provides the means to implement a gated version of translocation (FIG. 1e). The electrokinetic flow mediating the array assembly process may also be exploited for the alignment of elongated particles, such as DNA, near the surface of the electrode. In addition, the present invention permits the realization of methods to sort and separate particles.

Arrays of colloidal particles may be placed in designated areas and confined there until released or disassembled. The overall shape of the array may be delineated by UV-oxide patterning or, in real time, by shaping the pattern of illumination. This capability enables the definition of functionally distinct compartments, permanent or temporary, on the electrode surface. Arrays may be subjected to changes of shape imposed in real time, and they may be merged with other arrays (FIG. 1f or split into two or more subarrays or clusters (FIG. 1g, FIGS. 4a, 4b). In addition, the local state of order of the array as well as the lateral particle density may be reversibly adjusted by way of the external electric field or modified by addition of a second, chemically inert bead component.

The present invention also allows for the combination of fundamental operations to develop increasingly complex products and processes. Examples given herein describe the implementation of analytical procedures essential to a wide range of problems in materials science, pharmaceutical drug discovery, genomic mapping and sequencing technology. Important to the integration of these and other functionalities in a planar geometry is the capability, provided by the present invention, to impose temporary or permanent compartmentalization in order to spatially isolate concurrent processes or sequential steps in a protocol and the ability to manipulate sets of particles in a manner permitting the concatenation of analytical procedures that are performed in different designated areas on the substrate surfaces.

This invention is for a method and apparatus to direct the lateral motion and induce the assembly into planar arrays of cells on semiconductor surfaces in response to temporally and spatially varying electric fields and to projected patterns of illumination.

The response of different types of cells to variations in the frequency and voltage of the applied electric field and to specific patterns and changing intensity of illumination enables the on-cue assembly of multiple arrays of cells in any desired position on the substrate, and further enables the repositioning, disassembly and re-assembly and more generally the reconfiguration and segmentation of such arrays. Time-constant and time-varying illumination patterns are generated by an optically programmable illumination pattern generator may be used and can be based on a graphical representation of the pattern created on a personal computer.

The novel methodology of image cytometry introduced in the present invention relates to the general fields of molecular and cellular biology and has applications in the fields of diagnostics, genetic analysis, cell biology and drug discovery. The image cytometry facilitates a multiplicity of cell-based biological and biochemical procedures based on the quantitative analysis of images recorded from array of cells. As with Random Encoded Array Detection (READ) or Programmable Array Reconfiguration and Segmentation (PARSE), these assays are performed in a highly parallel format in a small volume of sample on the surface of a semiconductor wafer.

BRIEF DESCRIPTION OF DRAWINGS

Other objects, features and advantages of the invention discussed in the above brief explanation will be more clearly understood when taken together with the following detailed description of an embodiment which will be understood as being illustrative only, and the accompanying drawings reflecting aspects of that embodiment, in which:

FIGS. 3a and 3b are illustrations of the oxide profile of an Si/SiOx electrode;

FIG. 5 is a photograph of the lensing action of individual colloidal beads;

FIG. 7 is a photograph of the inclusion of spacer particles within bead clusters;

FIG. 8 is an illustration of binding assay variations;

FIG. 10 is an illustration of a planar array of bead-anchored probe-target complexes;

FIGS. 11a–11e are illustrations of DNA stretching in accordance with the present invention;

DETAILED DESCRIPTION OF THE PREFERRED EMBODIMENTS

Figure 1A:
FIGS. 1a–h are illustrations of the fundamental operations for bead manipulation.

The three functional elements of the present invention may be combined so as to provide a set of fundamental operations for the interactive spatial manipulation of colloidal particles and molecules, assembled into planar aggregates adjacent to an electrode surface. In the following description, fundamental operations in this "toolset" are described in order of increasing complexity. Specifically, it is useful to adopt a classification scheme based on the total number of inputs and outputs, or "terminals", involved in a given operation. For example, the merging of two separate arrays, or sets of particles, into one would be a "three-terminal" operation, involving two inputs and one output. The converse three-terminal operation, involving one input and two outputs, is the splitting of a given array into two subarrays.

Experimental conditions yielding the phenomena depicted in the various photographs included herein are as follows. An electrochemical cell is formed by a pair of planar ITO electrodes, composed of an ITO layer deposited on a glass substrate, or by a Si/SiOx electrode on the bottom and an ITO electrode on the top, separated by a typical gap of 50 microns or less. Given its dependence on the photoelectric properties of the Si/SiOx interface, light control is predicated on the use of a Si/SiOx electrode. Leads, in the form of platinum wires, are attached to the ITO and to the silicon electrode, which is first etched to remove the insulating oxide in the contact region, by means of silver epoxy. The cell is first assembled and then filled, relying on capillary action, with a suspension of colloidal beads, 1 or 2 microns in diameter, at a typical concentration of 0.1% solids in 0.1 mM azide solution, corresponding to approximately $2 \times 10^8$ particles per milliliter. The number is chosen so as to yield between ½ and 1 full monolayer of particles on the electrode surface. Anionic (e.g., carboxylated polystyrene, silica), cationic (e.g., aminated polystyrene) or nominally neutral (e.g., polystyrene) have all been used to demonstrate the basic phenomena underlying the three functional elements of the present invention. The silicon electrode was fabricated from a 1 inch-square portion of a Si (100) wafer, typically 200–250 microns thick, n-doped to typically 0.01 Ohm cm resistivity, and capped with a thin oxide of typically 30–40 Angstroms thickness. A thick oxide layer of typically 6000–8000 Angstrom thickness, grown under standard conditions in a furnace at 950 degrees C., may be etched by standard photolithography to define the structures of interest. Alternatively, a thin oxide layer may be regrown on a previously stripped surface of (100)-orientation under UV illumination. Given its ease of implementation and execution, UV-mediated oxide regrowth is the preferable technique: it provides the means to pattern the surface by placing a quartz mask representing the desired pattern in the path of UV illumination and it leaves a chemically homogeneous, topographically flat top surface. To avoid non-specific particle adsorption to the electrode surface, stringent conditions of cleanliness should be followed, such as those set forth in the General Experimental Conditions below.

Figure 2A:
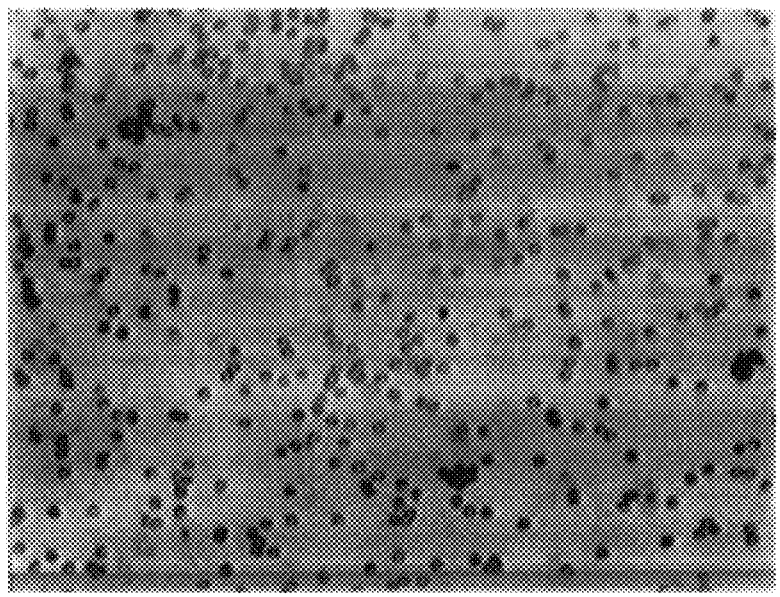
FIGS. 2a and 2b are photographs illustrating the process of capturing particles in designated areas on the substrate surface.
Figure 2B:
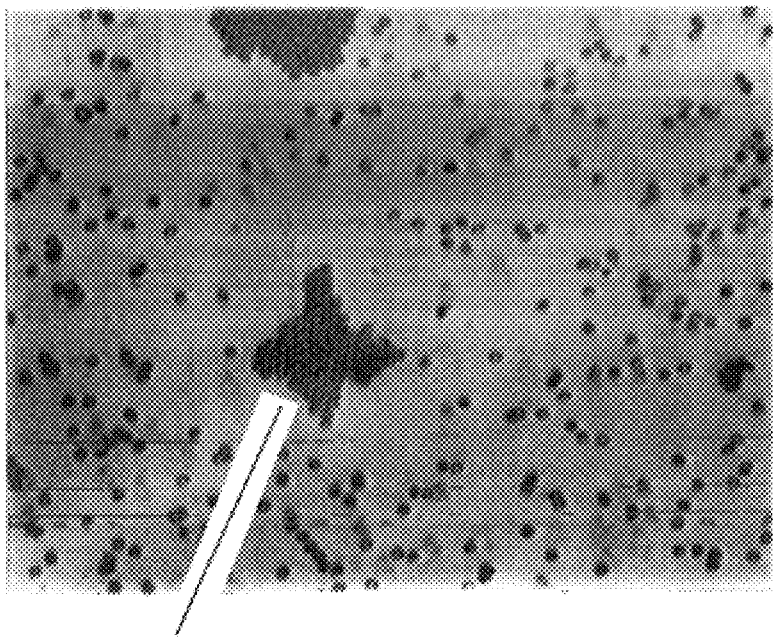

The fundamental one-terminal operation is a "capture-and-hold" operation (FIG. 1a) which forms an array of particles in a designated area of arbitrary outline on the surface that is delineated by UV-mediated oxide patterning or by a corresponding pattern of illumination projected on an otherwise uniform Si/SiOx substrate surface. FIGS. 2a and 2b illustrate bead capture on a surface characterized by a very thin oxide region 22 (approximately 20–30 Angstroms in thickness) and correspondingly low impedance, while the remaining surface is covered with the original, thick oxide with correspondingly high impedance. In FIG. 2a, there is no applied field, and hence, no bead capture. In contrast, in FIG. 2b, an electric field is applied (10Vp-p source, 1 kHz) and bead capture occurs within the thin oxide region 22. Under these conditions, an array starts to grow within less than a second and continues to grow over the next approximately 10 seconds as beads arrive from increasingly larger distances to add to the outward growing perimeter of region 22. Growth stops when the array approaches the outer limit of the delineated target area, i.e., the area defined by the thin oxide having a low impedance. The internal state of order of the captured aggregate of beads is determined by the strength of the applied voltage, higher values favoring increasingly denser packing of beads and the eventual formation of ordered arrays displaying a hexagonally crystalline configuration in the form of a bubble raft. The array remains in place as long as the applied voltage is present. Removal of the applied voltage results in the disassembly of the array.

The "capture-and-hold" operation may also be implemented under illumination with visible or infrared light, for example by simply projecting a mask patterned with the desired layout onto the Si/SiOx electrode. A regular 100 W quartz microscope illuminator has been used for this purpose on a Zeiss UEM microscope, with apertures or masks inserted in the intermediate image plane to provide the required shape in the plane of the electrode (when focused properly under conditions of Koehler illumination). Alternatively, an IR laser diode with output of 3 mW at 650–680 nm also has been used. The use of external illumination rather than oxide patterning for the spatial confinement of particles allows the confinement pattern to be easily modified.

Figure 1B:
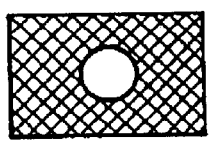
Figure 2C:
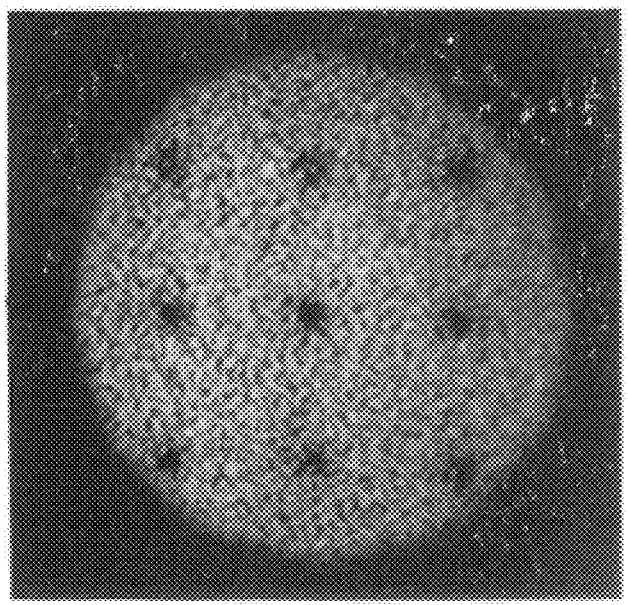
FIGS. 2c and 2d are photographs illustrating the process of excluding particles from designated areas on the substrate surface.
Figure 2D:
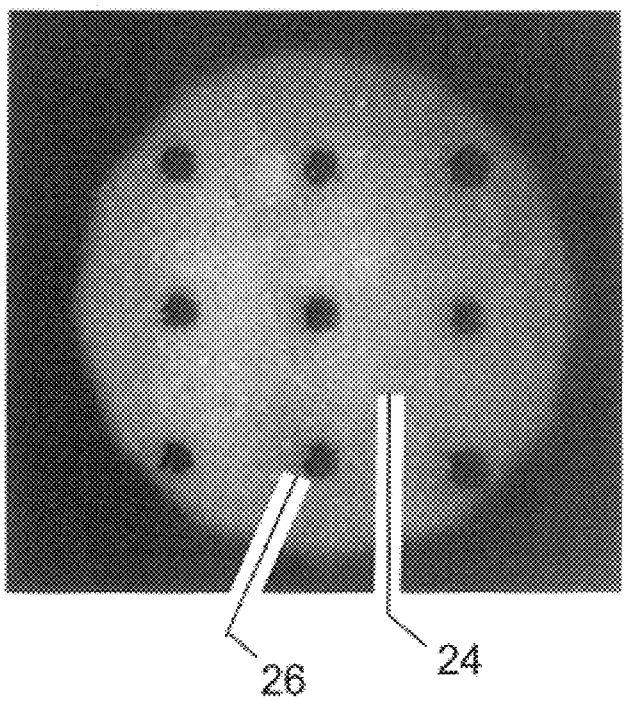

Related to "capture-and-hold" is the one-terminal operation of "exclude-and-hold" (FIG. 1b) which clears particles from a designated area on the surface. Increasing the frequency of the applied voltage to approximately 100 kHz leads to an inversion in the preference of particles which assemble in the thin-oxide portion of the surface (e.g., region 22, FIG. 2b) and instead form structures decorating the outside of the target area perimeter. Rather than relying on this effect, the exclusion of particles from the desired areas is also accomplished, in analogy to the original "capture-and-hold" operations, by simply embedding the corresponding structure in the Si/SiOx interface by UV-mediated oxide regrowth. In the example of FIGS. 2c and 2d, this is achieved, under conditions otherwise identical to those described above, with respect to FIGS. 2a and 2b, by applying 20V (pp) at 10 kHz. While the oxide thickness in the non designated areas 24 is approximately 30 Angstroms, the value in the designated square areas 26 is approximately 40 Angstroms, implying a correspondingly higher impedance at the applied frequency.

The "capture-and-hold" operation enables the spatial compartmentalization of the substrate surface into functionally distinct regions. For example, particles of distinct chemical type, introduced into the electrochemical cell at different times or injected in different locations, can be kept in spatially isolated locations by utilizing this operation.

Figure 1C:

The fundamental two-terminal operation is translocation (FIG. 1c), or the controlled transport of a set of particles from location O to location F on the surface; here, O and F are target areas to which the above-described one-terminal operations may be applied. The one-dimensional, lateral bead transport used in translocation is achieved by imposing a lateral current along a conduit connecting areas O and F, as shown in FIGS. 3a and 3b or by projecting a corresponding linear pattern of illumination. In this channeling operation, beads move in the direction of lower impedance in the direction of the arrow shown in FIGS. 3a and 3b, in accordance with the underlying electrokinetic flow.

Figure 3C:
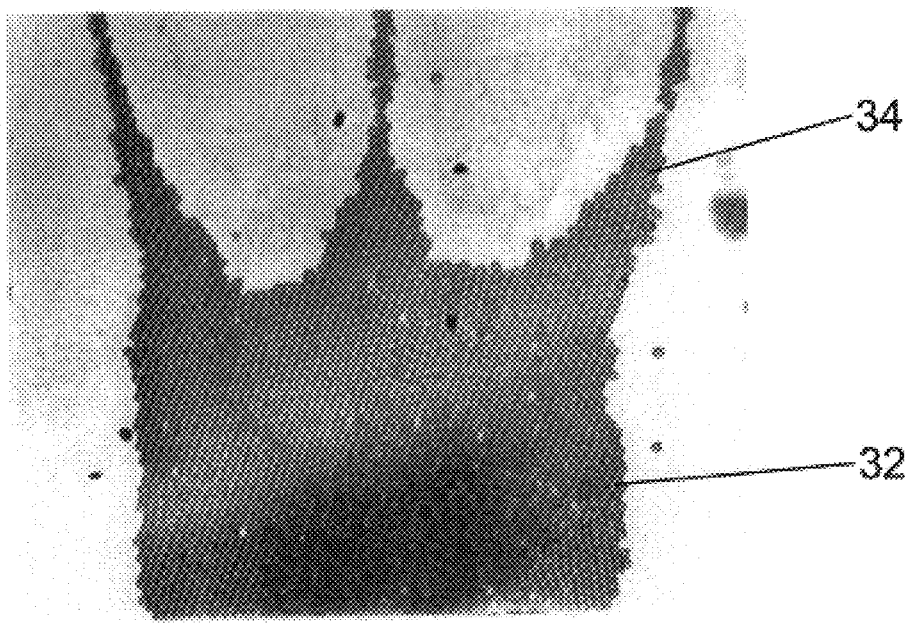
FIGS. 3c and 3d are photographs of the channeling of particles along conduits.
Figure 3D:
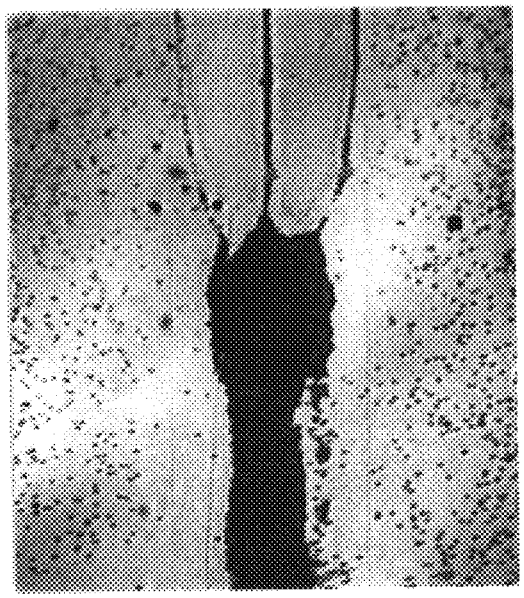

Oxide patterning may be utilized in two ways to create a lateral current along the Si/SiOx interface. The simplest method is depicted in FIG. 3c and shows a large open holding area 32 fed by three narrow conduits 34 defined by etching a thermal oxide. Beads move to the holding area 32 along the narrow conduits 34 to form a bead array. FIG. 3d is a large scale view of the array of FIG. 3c. The principle invoked in creating transport is that of changing the aspect ratio (narrow conduit connected to wide holding area) of the embedded pattern with constant values of thin oxide thickness inside and thick oxide outside, as illustrated in FIG. 3a. In FIGS. 3c and 3d, the applied voltage was 10V (pp) at 10 kHz. An alternative approach for creating bead transport, enabled by UV-mediated oxide regrowth, is to vary the oxide thickness along the conduit in a controlled fashion. This is readily accomplished by UV exposure through a graduated filter. Differences in the oxide thickness between O and F of as little as 5–10 Angstroms suffice to effect lateral transport. In this situation, the aspect ratio of the conduit and holding areas need not be altered. This is illustrated in FIG. 3b.

The use of external illumination to define conduits, by varying the illumination intensity along the conduit to create the requisite impedance gradient, has the advantage that the conduit is only a temporary structure, and that the direction of motion may be modified or reversed if so desired. The present invention provides for mechanisms of light-mediated active linear transport of planar aggregates of beads under interactive control. This is achieved by adjusting an external pattern of illumination in real time, either by moving the pattern across the substrate surface in such a way as to entrain the illuminated bead array or by electronically modulating the shape of the pattern to induce motion of particles.

Two modes of light-mediated, active transport are:
i) Direct Translocation ("tractor beam") which is a method of translocating arrays and of delineating their overall shape by adjusting parameters so as to favor particle assembly within illuminated areas of the surface, as described herein. Arrays simply follow the imposed pattern. The rate of motion is limited by the mobility of particles in the fluid and thus depends on particle diameter and fluid viscosity.
ii) Transverse Array Constriction is a bead transport mechanism related to peristaltic pumping of fluids through flexible tubing. The light-control component of the present invention may be used for a simple implementation of this very general concept. A multi-component planar aggregate of beads is confined to a rectangular channel, by UV-patterning if so desired, or simply by light. Beads are free to move along the channel by diffusion (in either direction). An illumination pattern matching the transverse channel dimension is set up and is then varied in time so as to produce a transverse constriction wave that travels in one direction along the channel. Such a constriction wave may be set up in several ways. A conceptually simple method is to project a constricting mask onto the sample and move the projected mask pattern in the desired fashion. This method also may be implemented electronically by controlling the illumination pattern of a suitable array of light sources, thus obviating the need for moving parts in the optical train.

The control of lateral bead transport by changing or moving patterns of illumination has the advantage that it may be applied whenever and wherever (on a given substrate surface) required, without the need to impose gradients in impedance by predefined UV patterning. On the other hand, a predefined impedance pattern can provide additional capabilities in conjunction with light-control. For example, it may be desirable to transport beads against a substrate-embedded impedance gradient to separate beads on the basis of mobility.

Figure 1D:
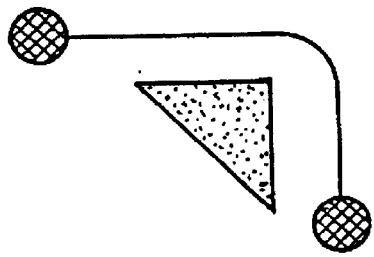
Figure 1E:

Conduits connecting O and F need not be straight: as with tracks directing the motion of trains, conduits may be shaped in any desirable fashion (FIG. 1d). A gated version of translocation (FIG. 1e) permits the transport of particles from O to F only after the conduit is opened (or formed in real time) by a gating signal. This operation utilizes UV oxide patterning to establish two holding areas, O and F, and also light control to temporarily establish a conduit connecting O and F. An alternative implementation is based on an oxide embedded impedance gradient. A zone along the conduit is illuminated with sufficiently high intensity to keep out particles, thereby blocking the passage. Removal (or reduction in intensity) of the illumination opens the conduit. In the former case, light enables the transport of beads, while in the latter case, light prevents the transport of beads.

Figure 1F:
Figure 1G:

The fundamental three-terminal operations are the merging and splitting of sets or arrays of beads (FIGS. 1f and 1g). The merging of two arrays (FIG. 1f) involves the previous two fundamental operations of "capture-and-hold", applied to two spatially isolated sets of beads in locations O1 and O2, and their respective channeling along merging conduits into a common target area, and their eventual channeling, subsequent to mixing, or a chemical reaction, into the final destination, a third holding area, F. This is accomplished, under the conditions stated above, by invoking one-terminal and gated two-terminal operations.

The splitting of an array into two subarrays (FIG. 1g) is a special case of a generally more complex sorting operation. Sorting involves the classification of beads in a given set or array into one of two subsets, for example according to their fluorescence intensity. In the simpler special case, a given array, held in area O, is to be split into two subarrays along a demarcation line, and subarrays are to be moved to target areas F1 and F2. Under the conditions stated above, this is accomplished by applying the "capture-and-hold" operation to the array in O. Conduits connect O to F1 and F2. High intensity illumination along a narrowly focused line serves to divide the array in a defined fashion, again relying on gated translocation to control transport along conduits away from the holding area O. An even simpler version, termed indiscriminate splitting, randomly assigns particles into F1 and F2 by gated translocation of the array in O into F1 and F2 after conduits are opened as described above.

Figure 4A:
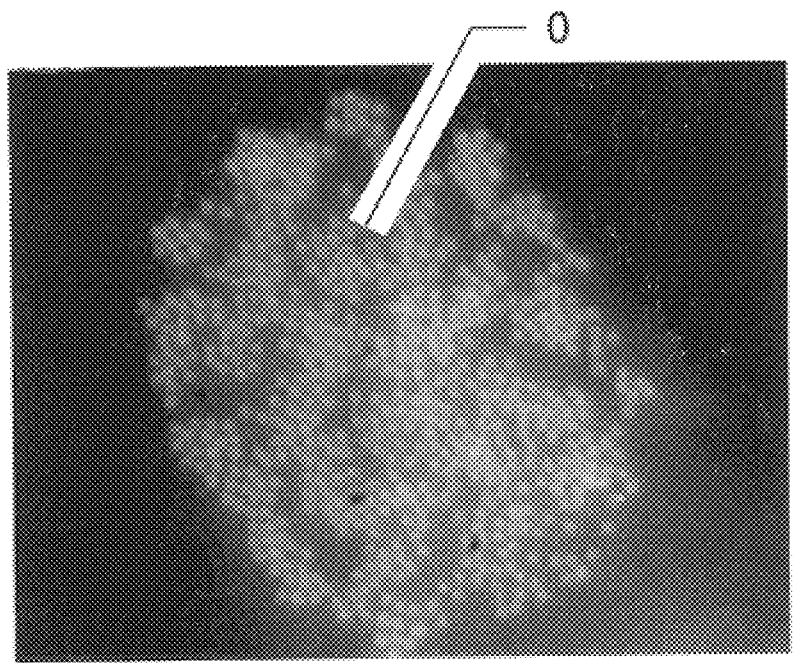
FIGS. 4a and 4b are photographs of the splitting of an existing aggregate into small clusters.
Figure 4B:
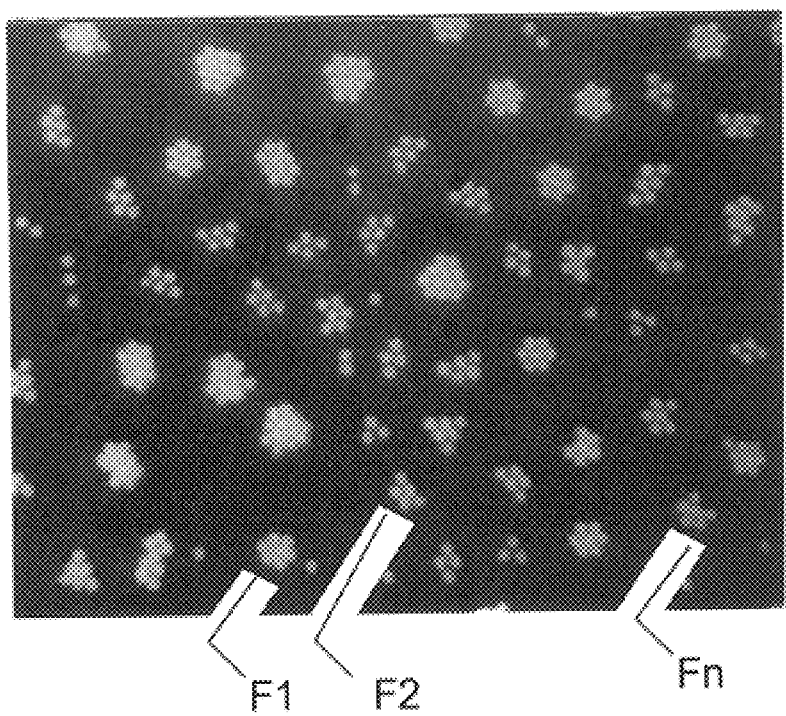

FIGS. 4a and 4b show a variant in which beads in region O (FIG. 4a) are split into multiple regions F1, F2, . . . Fn (FIG. 4b). This reversible splitting of an aggregate or array into n subarrays, or clusters, is accomplished, for carboxylated polystyrene spheres of 2 micron diameter at a concentration corresponding to an electrode coverage of a small fraction of a monolayer, at a frequency of 500 Hz, by raising the applied voltage from typically 5V (pp) to 20V (pp). This fragmentation of an array into smaller clusters reflects the effect of a field-induced particle polarization. The splitting is useful to distribute particles in an array over a wider area of substrate for presentation to possible analytes in solution, and for subsequent scanning of the individual clusters with analytical instruments to make individual readings.

Figure 1H:
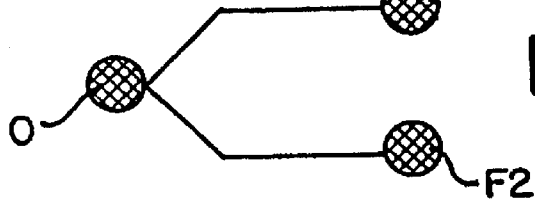

The three functional elements of the present invention described herein may be also combined to yield additional fundamental operations to control the orientation of anisotropic objects embedded in the electroosmotic flow created by the applied electric field at the electrode surface. The direction of the flow, in the plane of the substrate, is controlled by gradients in the impedance that are shaped in the manner described in connection with the channeling operation. This is used to controllably align anisotropic objects as illustrated in FIG. 1h, and may be applied to stretch out and align biomolecules, such as DNA.

An additional fundamental operation that complements the previous set is that of permanently anchoring an array to the substrate. This is best accomplished by invoking anchoring chemistries analogous to those relying on heterobifunctional cross-linking agents invoked to anchor proteins via amide bond formation. Molecular recognition, for example between biotinylated particles and surface-anchored streptavidin, provides another class of coupling chemistries for permanent anchoring.

General Experimental Conditions

The functional elements, namely the electric-field induced assembly of planar particle arrays, the spatial modulation of the interfacial impedance by means of UV-mediated oxide or surface-chemical patterning and finally, the control over the state of the interfacial impedance by light which are used in the present invention, have been demonstrated in experimental studies. These studies employed n-doped silicon wafers (resistivities in the range of 0.01 Ohm cm), capped with either thermally grown oxide layers of several thousand Angstrom thickness, or with thin oxide layers, regrown after removal of the original "native" oxide in HF, under UV illumination from a deuterium source in the presence of oxygen to typical thicknesses between 10 and 50 Angstroms. Lithographic patterning of thermally grown oxide employed standard procedures implemented on a bench top (rather than a clean room) to produce features in the range of several microns.

Surfaces were carefully cleaned in adherence with industry standard RCA and Piranha cleaning protocols. Substrates were stored in water produced by a Millipore water purification system prior to use. Surfaces were characterized by measuring the contact angle exhibited by a 20 microliter droplet of water placed on the surface and viewed (from the side) through a telescope. The contact angle is defined as the angle subtended by the surface and the tangent to the droplet contour (in side view) at the point of contact with the surface. For example, a perfectly hemispherical droplet shape would correspond to a contact angle of 90 degrees. Surface chemical derivatization with mercapto-propyl-trimethoxysilane (2% in dry toluene) produced surfaces giving typical contact angles of 70 degrees. Oxidation of the terminal thiol functionality under UV irradiation in the presence of oxygen reduced the contact angle to zero in less than 10 min of exposure to UV from the deuterium source. Other silane reagents were used in a similar manner to produce hydrophobic surfaces, characterized by contact angles in excess of 110 degrees.

Simple "sandwich" electrochemical cells were constructed by employing kapton film as a spacer between Si/SiOx and conductive indium tin oxide (ITO), deposited on a thin glass substrate. Contacts to platinum leads were made with silver epoxy directly to the top of the ITO electrode and to the (oxide-stripped) backside of the Si electrode. In this two-electrode configuration, AC fields were produced by a function generator, with applied voltages ranging up to 20V and frequencies varying from DC to 1 MHZ, high frequencies favoring the formation of particle chains connecting the electrodes. Currents were monitored with a potentiostat and displayed on an oscilloscope. For convenience, epi-fluorescence as well as reflection differential interference contrast microscopy employed laser illumination. Light-induced modulations in EIS impedance were also produced with a simple 100 W microscope illuminator as well as with a 3 mW laser diode emitting light at 650–680 nm.

Colloidal beads, both anionic and cationic as well as nominally neutral, with a diameter in the range from several hundred Angstroms to 20 microns, stored in a $NaN_2$ solution, were employed.

Close attention was paid to colloidal stability to avoid non-specific interactions between particles and between particles and the electrode surface. Bacterial contamination of colloidal suspensions was scrupulously avoided.

Typical operating conditions producing, unless otherwise indicated, most of the results described herein, were: 0.2 mM $NaN_2$ (sodium azide) solutions, containing particles at a concentration so as to produce not more than a complete monolayer of particles when deposited on the electrode; applied DC potentials in the range of 1–4V, and AC potentials in the range of 1–10V (peak-to-peak) and 500 Hz–10 kHz, with an electrode gap of 50 microns; anionic (carboxylated polystyrene) beads of 2 micron diameter, as well as (nominally neutral) polystyrene beads of 2–20 micron diameter.

The method and apparatus of the present invention may be used in several different areas, examples of which are discussed in detail. Each example includes background information followed by the application of the present invention to that particular application.

EXAMPLE I

Fabrication of Surfaces and Coatings with Designed Properties

The present invention may be used to fabricate planar surfaces and coatings with designed properties. Specifically, the functional elements of the present invention enable the formation of arrays composed of particles of a wide range of sizes (approximately 100 Angstrom to 10 microns) and chemical composition or surface functionality in response to AC or DC electric fields. These arrays may be placed and delineated in designated areas of the substrate, and the interparticle spacing and internal state of order within the array may be controlled by adjusting the applied field prior to anchoring the array to the substrate. The newly formed surfaces display pre-designed mechanical, optical and chemical characteristics, and they may be subjected to further modification by subsequent treatment such as chemical cross-inking.

The mechanical and/or chemical modification of surfaces and coatings principally determines the interaction between materials in a wide range of applications that depend on low adhesion (e.g., the familiar "non-stick" surfaces important in housewares) or low friction (e.g., to reduce wear in computer hard disks), hydrophobicity (the tendency to repel water, e.g., of certain fabrics), catalytic activity or specific chemical functionality to either suppress molecular interactions with surfaces or to promote them. The latter area is of particular importance to the development of reliable and durable biosensors and bioelectronic devices. Finally, a large number of applications depend on surfaces of defined topography and/or chemical functionality to act as templates controlling the growth morphology of deposited materials or as "command surfaces" directing the alignment of optically active molecules in deposited thin organic films, as in liquid crystal display applications.

Extensive research has been devoted to the formation of surfaces by adsorption of thin organic films of known composition from the liquid or gas phase by several methods. Notwithstanding their seeming simplicity and widespread use, these methods can be difficult to handle in producing reliable and reproducible results. In addition, molecular films are not well suited to produce surfaces displaying a regular topography.

An alternative approach to the problem is the modification of conductive surfaces by electrophoretic deposition of suspended particulates. This is a widely used technique in industrial settings to produce paint coatings of metal parts, and to deposit phosphor for display screens. The active deposition process significantly enhances the kinetics of formation (in contrast to passive adsorption of organic films from solution), an important consideration in practical applications. Electrophoretic deposition requires high DC electric fields and produces layers in which particles are permanently adsorbed to the surface. While particles in so-deposited monolayers are usually randomly distributed, the formation of polycrystalline monolayers of small (150 Angstrom) gold colloids on carbon-coated copper grids is also known. However, the use of carbon-coated copper grids as substrates is not desirable in most applications.

Prior art methods have been described for the formation of ordered planar arrays of particles under certain conditions. For example, the formation of ordered colloidal arrays in response to AC electric fields on conductive indium tin oxide (ITO) electrodes is known. However, the resulting layers were composed of small patches of ordered arrays, randomly distributed over the surface of the otherwise bare ITO substrate. Arrays of monodisperse colloidal beads and globular proteins also have been previously fabricated by using convective flow and capillary forces. However, this latter process has the disadvantage of leaving deposited particle arrays immobilized and exposed to air, making it difficult to modify arrays by subsequent liquid phase chemistry.

The present invention provides a method of forming planar arrays with precise control over the mechanical, optical and chemical properties of the newly created layer. This method has several distinct advantages over the prior art. These result from the combination of AC electric field-induced array formation on insulating electrodes (Si/SiOx) that are patterned by UV-mediated oxide regrowth. The process of the present invention enables the formation of ordered planar arrays from the liquid phase (in which particles are originally suspended) in designated positions, and in accordance with a given overall outline. This eliminates the above-stated disadvantages of the prior art, i.e., dry state, irregular or no topography, random placement within an aggregate, immobilization of particles and uncontrolled, random placement of ordered patches on the substrate.

An advantage of the present invention is that arrays are maintained by the applied electric field in a liquid environment. The process leaves the array in a state that may be readily disassembled, subjected to further chemical modification such as cross-linking, or made permanent by chemical anchoring to the substrate. Furthermore, the liquid environment is favorable to ensure the proper functioning of many proteins and protein supramolecular assemblies of which arrays may be composed. It also facilitates the subsequent liquid-phase deposition of additional layers of molecules (by chemical binding to beads or proteins in the deposited layer), the cycling of arrays between states of different density and internal order (including complete disassembly of the array) in response to electric fields and the chemical cross-linking of particles into two-dimensionally connected layers, or gels, formed, for example, of chemically functionalized silica spheres. The present invention can be practiced on insulating electrodes such as oxide-capped silicon, to minimize Faradaic processes that might adversely affect chemical reactions involved in the gelation process or in anchoring the array to the substrate. The use of Si/SiOx electrodes also enables the control of array placement by external illumination.

The formation of colloidal arrays composed of small particles in accordance with the present invention provides a route to the fabrication of surfaces with relief structure on the scale of the particle diameter. Aside from their optical properties, such "micro-rough" surfaces are of interest as substrates for the deposition of DNA in such a way as to alleviate steric constraints and thus to facilitate enzyme access.

Particles to which the invention applies include silica spheres, polymer colloids, lipid vesicles (and related assemblies) containing membrane proteins such as bacteriorhodopsin $(bR)^-$ a light-driven proton pump that can be extracted in the form of membrane patches and disks or vesicles. Structured and functionalized surfaces composed of photoactive pigments are of interest in the context of providing elements of planar optical devices for the development of innovative display and memory technology. Other areas of potential impact of topographically structured and chemically functionalized surfaces are the fabrication of template surfaces for the controlled nucleation of deposited layer growth and command surfaces for liquid crystal alignment. The present invention also enables the fabrication of randomly heterogeneous composite surfaces. For example, the formation of arrays composed of a mixture of hydrophobic and hydrophilic beads of the same size creates a surface whose wetting and lubrication characteristics may be controlled by the composition of the deposited mixed bead array. In this way, the location of the individual beads is random, but the relative proportion of each type of bead within the array is controllable.

EXAMPLE II

Assembly of Lens Arrays and Optical Diffraction Elements

The present invention can be used to fabricate lens arrays and other surface-mounted optical elements such as diffraction gratings. The functional elements of the present invention enable the placement and delineation of these elements on ITO, facilitating integration with existing planar display technology, and on Si/SiOx, facilitating integration with existing silicon-based device technology.

Silica or other oxide particles, polymer latex beads or other objects of high refractive index suspended in an aqueous solution, will refract light. Ordered planar arrays of beads also diffract visible light, generating a characteristic diffraction pattern of sharp spots. This effect forms the basis of holographic techniques in optical information processing applications.

A. The present invention provides for the use of arrays of refractive colloidal beads as light collection elements in planar array formats in conjunction with low light level detection and CCD imaging. CCD and related area detection schemes will benefit from the enhanced light collection efficiency in solid-phase fluorescence or luminescence binding assays.

This assay format relies on the detection of a fluorescence signal indicating the binding of probes to bead-anchored targets in the vicinity of the detector. To maximize throughput, it is desirable to monitor simultaneously as many binding events as possible. It is here that array formation by the methods of the present invention is particularly valuable because it facilitates the placement and tight packing of beads in the target area monitored by the CCD detector, while simultaneously providing for the additional benefit of lensing action and the resulting increase in light collection efficiency.

Increased collection efficiency has been demonstrated in experiments employing individual, large (10 micron diameter) polystyrene beads as lensing elements to image small (1 micron diameter) fluorescent polystyrene beads. Under the experimental conditions set forth above an applied voltage of 5V (pp) at 300 Hz induced the collection of small particles under individual large beads within a second. This is shown in FIG. 5, where small beads alone, e.g., 52, appear dim, whereas small beads, e.g., 54, gathered under a large bead 56 appear brighter and magnified. The small beads redisperse when the voltage is turned off.

B. The use of colloidal bead arrays as diffraction gratings and thus as holographic elements is known. Diffraction gratings have the property of diffracting light over a narrow range of wavelengths so that, for given angle of incidence and wavelength of the illuminating light, the array will pass only a specific wavelength (or a narrow band of wavelengths centered on the nominal value) that is determined by the inter-particle spacing. Widely discussed applications of diffraction gratings range from simple wavelength filtering to the more demanding realization of spatial filters and related holographic elements that are essential in optical information processing.

The present invention provides for a rapid and well controlled process of forming planar arrays in a state of crystalline order which will function as surface-mounted optical diffraction elements. In addition, the resulting surfaces may be designed to display topographical relief to enhance wave-length selective reflectivity. These arrays may be formed in designated areas on a substrate surface. In contrast to the slow and cumbersome prior art method of fabricating such arrays by way of forming equilibrium crystals in aqueous solutions of low salt content, the present invention provides a novel approach to rapidly and reliably fabricate particle arrays at a solid-liquid interface. This approach relies on field-induced formation of arrays to trigger the process, and on UV-mediated patterning or light control to position and shape the arrays. In addition, the inter-particle distance, and internal state of order, and hence the diffraction characteristics of the array, may be fine-tuned by adjusting the applied electric field. For example, a field-induced, reversible order-disorder transition in the array will alter the diffraction pattern from one composed of sharp spots to one composed of a diffuse ring. The assembly of such arrays on the surface of silicon wafers, as described herein, provides a direct method of integration into existing microelectronic designs. Arrays may be locked in place by chemical coupling to the substrate surface, or by relying on van der Waals attraction between beads and substrate.

EXAMPLE III

A Novel Mechanism for the Realization of a Particle-Based Display

The present invention provides the elements to implement lateral particle motion as a novel approach to the realization of a particle-based display. The elements of the present invention provide for the control of the lateral motion of small particles in the presence of a pre-formed lens array composed of large, refractive particles.

Colloidal particulates have been previously employed in flat-panel display technology. The operating principle of these designs is based on electrophoretic motion of pigments in a colored fluid confined between two planar electrodes. In the OFF (dark) state, pigments are suspended in the fluid, and the color of the fluid defines the appearance of the display in that state. To attain the ON (bright) state, particles are assembled near the front (transparent) electrode under the action of an electric field. In this latter state, incident light is reflected by the layer of particles assembled near the electrode, and the display appears bright. Prototype displays employing small reflective particles in accordance with this design are known. However, these displays suffered from a number of serious problems including: electrochemical degradation and lack of colloidal stability as a result of prolonged exposure to the high DC electric fields required to achieve acceptable switching speeds; and non-uniformities introduced by particle migration in response to field gradients inherent in the design of the addressing scheme.

The present invention provides a novel mechanism for the design of a particle-based display which takes advantage of electric field-induced array formation as well as controlled, field-induced lateral particle displacements. First, a lens array composed of colloidal beads is formed. This lens array also serves as a spacer array to maintain a well-defined gap between the bottom electrode and the top electrode that may now be placed over the (pre-formed) array. This facilitates fabrication of uniform flat panel displays with a narrow gap that is determined by the particle diameter.

Next, small colloidal particles are added to the electrolyte solution in the gap. These may be fluorescent, or may be reflecting incident white light. Under the action of an AC electric field of appropriate frequency, these small particles can be moved laterally to assemble preferentially within the footprint of a larger bead. When viewed through a larger bead, small fluorescent beads assembled under a large bead appear bright as a result of the increased light collection efficiency provided by the lensing action of the large bead; this is the ON state (FIG. 5). When moved outside the footprint of the larger bead, particles appear dim, and may be made entirely invisible by appropriate masking; this is the OFF state. The requisite lateral particle motion may be induced by a change in the applied voltage or a change in light intensity. Each large or lensing bead introduces a lateral nonuniformity in the current distribution within the electrolyte because the current is perturbed by the presence of each lensing bead.

In contrast to the prior art displays, the present invention employs AC, not DC fields, and insulating (rather than conductive) electrodes, thereby minimizing electrochemical degradation. The lateral non-uniformity introduced by the lens array is desirable because it introduces lateral gradients in the current distribution within the display cell. These gradients mediate the lateral motion of small beads over short characteristic distances set by the diameter of the large lensing beads, to effect a switching between ON and OFF states. Thus, the present invention readily accommodates existing technology for active matrix addressing.

EXAMPLE IV

Separation and Sorting of Beads and Particles

The present invention can be used to implement several procedures for the separation and sorting of colloidal particles and biomolecules in a planar geometry. Specifically, these include techniques of lateral separation of beads in mixtures. Individual beads may be removed from an array formed in response to an electric field by the application of optical tweezers.

The separation of components in a given mixture of chemical compounds is a fundamental task of analytical chemistry. Similarly, biochemical analysis frequently calls for the separation of biomolecules, beads or cells according to size and/or surface charge by electrophoretic techniques, while the sorting (most commonly into just two sub-classes) of suspended cells or whole chromosomes according to optical properties such as fluorescence emission is usually performed using field-flow fractionation including flow cytometry and fluorescence-activated cell sorting.

In a planar geometry, bead mixtures undergoing diffusion have been previously separated according to mobility by application of an AC electric field in conjunction with lithographic patterning of the electrode surface designed to promote directional drift. Essentially, as described in U.S. Pat. No. 5,593,565 to Ajdari et al., the contents of which are included herein by reference, the AC or pulsing electric field is used to move small beads in a particular direction over a period of time, advancing beads of higher mobility relative to those of lower mobility. Capillary electrophoresis has been implemented in a planar geometry, see e.g., B. B. Haab and R. A. Mathies, Anal. Chem 67, 3253–3260 (1995), the contents of which are incorporated herein by reference.

Figure 9A:
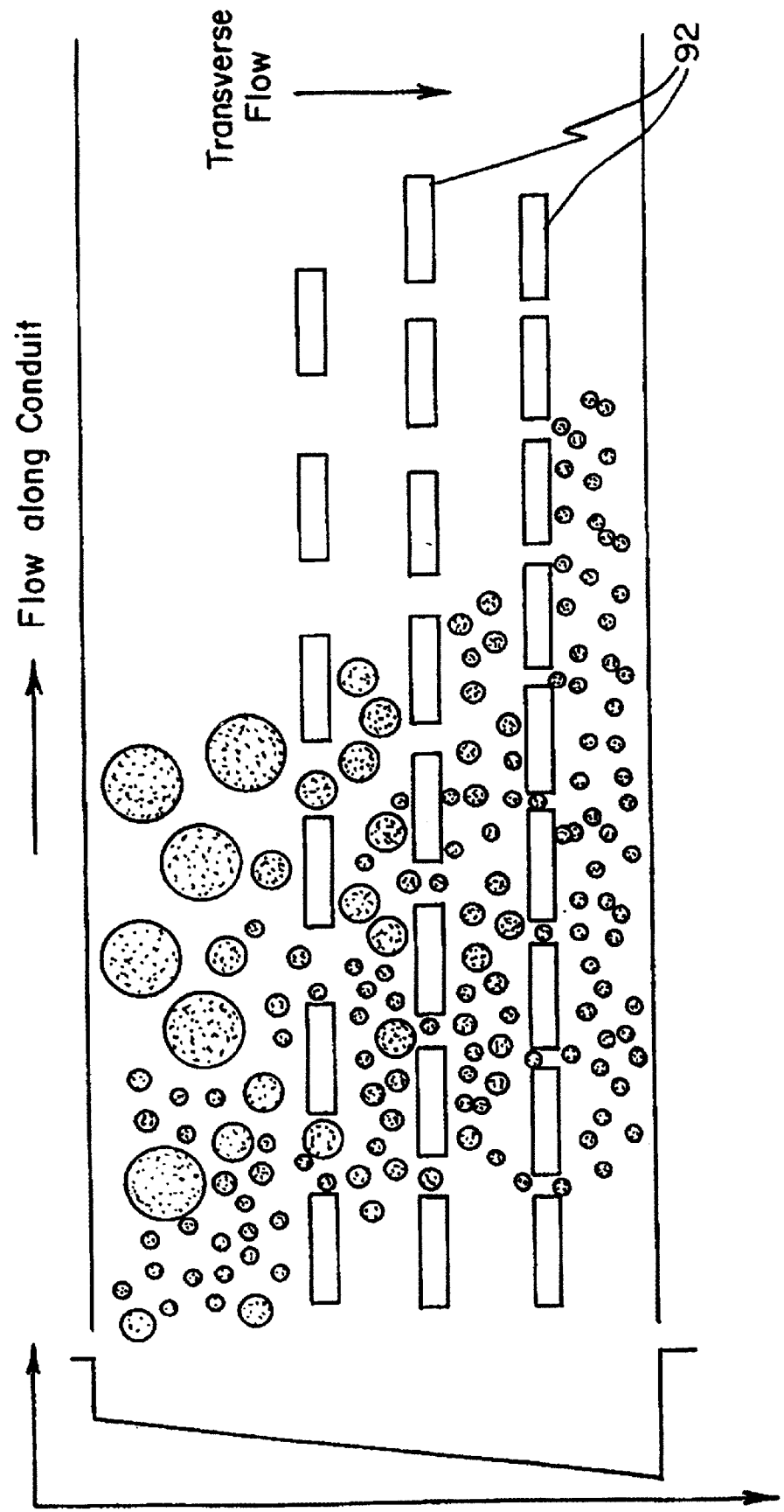
FIGS. 9a and 9b are illustrations of two mechanisms of particle sorting.

The methods of the present invention may be applied in several ways to implement the task of separation, sorting or isolation in a planar geometry. In contrast to the prior art approaches, the present invention provides a significant degree of flexibility in selecting from among several available procedures, the one best suited to the particular task at hand. In some cases, more than one separation technique may be applied, and this provides the basis for the implementation of two-dimensional separation. That is, beads may be separated according to two different physical-chemical characteristics. For example, beads may first be separated by size and subsequently, by raising the applied frequency to induce chain formation, by polarizability. This flexibility offers particular advantages in the context of integrating analytical functionalities in a planar geometry. Several techniques will now be described.

i) The present invention may be used to implement "sieving" in lateral, electric field-induced flow on surfaces patterned by UV-mediated oxide regrowth to sort beads in a mixture by size. The fundamental operations of the invention are invoked to set up directed lateral particle motion along conduits laid out by UV-mediated oxide regrowth. Conduits are designed to contain successively narrower constrictions through which particles must pass. Successively finer stages allow only successively smaller particles to pass in this "sieving" mechanism (FIG. 9a). As shown in FIG. 9a, the primary particle flow is in the direction left to right, while a transverse flow is established in the top to bottom direction utilizing an oxide profile as shown. Additionally, rows of barriers 92 made from thick oxide are positioned along the conduit with the spacing between the barriers in each row decreasing in the transverse direction. As the particles move along the conduit, the rows of barriers act to separate out smaller particles in the transverse direction. In contrast to previous methods based on electrophoretic separation, large DC electric fields, and the attendant potential problem of electrolysis and interference from electroosmotic flow in a direction opposite to the field-directed particle transport, the present invention uses AC electric fields and lateral gradients in interfacial impedance to produce transport. The present method has the advantage of avoiding electrolysis and it takes explicit advantage of electroosmotic flow to produce and control particle transport.

In addition, the use of Si/SiOx electrodes enables the use of the light-control component of the present invention to modify lateral transport of beads in real time. For example, external illumination may be employed to locally neutralize the lateral impedance gradient induced by UV-mediated oxide regrowth. Particles in these neutral "zones" would no longer experience any net force and come to rest. This principle may be used as a basis for the implementation of a scheme to locally concentrate particles into sharp bands and thereby to improve resolution in subsequent separation.

ii) The present invention may be used to implement "zone refining", a process of excluding minority components of a mixture by size or shape from a growing crystalline array of majority component. This process explicitly depends on the capabilities of the present invention to induce directional crystallization.

The process of zone refining is employed with great success in producing large single crystals of silicon of very high purity by excluding impurities from the host lattice. The concept is familiar from the standard chemical procedure of purification by re-crystallization in which atoms or molecules that are sufficiently different in size, shape or charge from the host species so as not to fit into the forming host crystal lattice as a substitutional impurity, are ejected into solution.

By enabling the growth of planar arrays, in a given direction and at a controlled rate, the present invention facilitates the implementation of an analogous zone refining process for planar arrays. The most basic geometry is the linear geometry. A multi-component mixture of beads of different sizes and/or shapes is first captured in a rectangular holding area on the surface, laid out by UV-patterning. Next, crystallization is initiated at one end of the holding area by illumination and allowed to slowly advance across the entire holding area in response to an advancing pattern of illumination. In general, differences of approximately 10% in bead radius trigger ejection.

iii) The present invention may be used to implement fractionation in a transverse flow in a manner that separates particles according to mobility.

Field-flow fractionation refers to an entire class of techniques that are in wide use for the separation of molecules or suspended particles. The principle is to separate particles subjected to fluid flow in a field acting transverse to the flow. A category of such techniques is subsumed under the heading of electric-field flow fractionation of which free-flow electrophoresis is a pertinent example because it is compatible with a planar geometry. Free-flow electrophoresis employs the continuous flow of a replenished buffer between two narrowly spaced plates in the presence of a DC electric field that is applied in the plane of the bounding plates transverse to the direction of fluid flow. As they traverse the electric field, charged particles are deflected in proportion to their electrophoretic mobility and collected in separate outlets for subsequent analysis. In contrast to conventional electrophoresis, free-flow electrophoresis is a continuous process with high throughput and it requires no supporting medium such as a gel.

The present invention enables the implementation of field-flow fractionation in a planar geometry. As previously discussed herein, impedance gradients imposed by UV-oxide profiling serve to mediate particle motion along the electrode surface in response to the external electric field. In a cell with a narrow gap, the resulting electrokinetic flow has a "plug" profile and this has the advantage of exposing all particles to identical values of the flow velocity field, thereby minimizing band distortions introduced by the parabolic velocity profile of the laminar flow typically employed in free-flow electrophoresis.

A second flow field, transverse to the primary flow direction, may be employed to mediate particle separation. This deflecting flow may be generated in response to a second impedance gradient. A convenient method of imposing this second gradient is to take advantage of UV-oxide patterning to design appropriate flow fields. Both longitudinal and transverse flow would be recirculating and thus permit continuous operation even in a closed cell, in contrast to any related prior art technique.

Figure 9B:
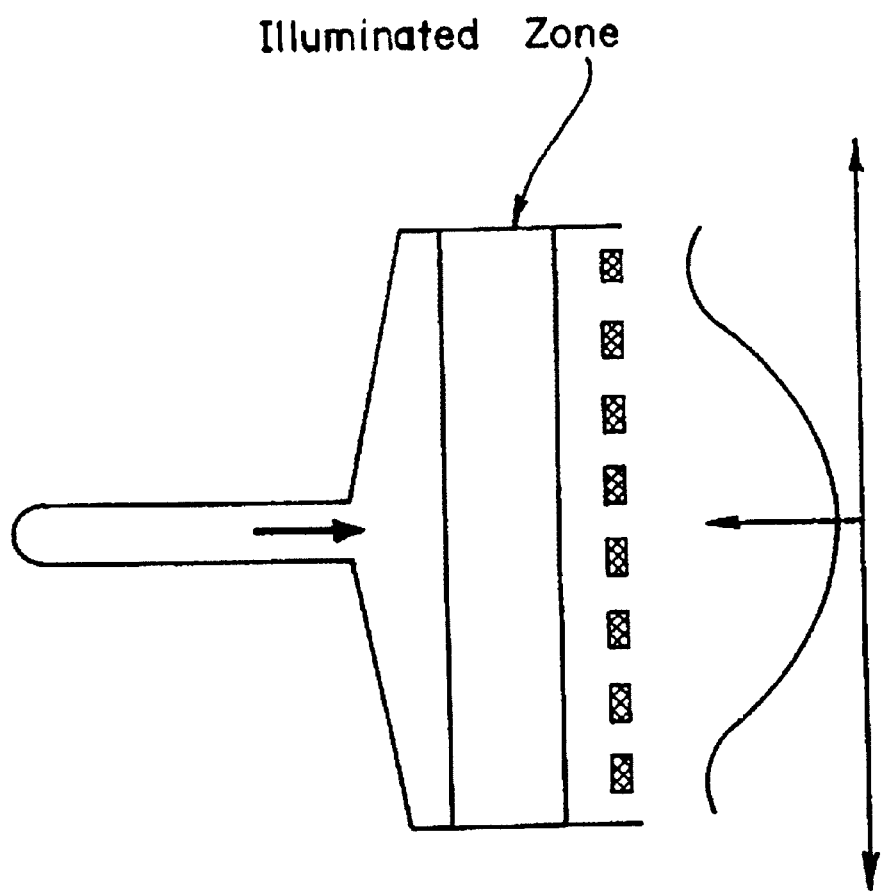
Figure 9C:
FIG. 9c is an illustration of the oxide profile of FIG. 9b.

Additional flexibility is afforded by invoking the light-control component of the present invention to illuminate the substrate with a stationary pattern whose intensity profile in the direction transverse to the primary fluid flow is designed to induce the desired impedance gradient and hence produce a transverse fluid flow. (FIG. 9b). This has the significant advantage of permitting selective activation of the transverse flow in response to the detection of a fluorescent bead crossing a monitoring window upstream. Non-fluorescent beads would not activate the transverse flow and would not be deflected. This procedure represents a planar analog of flow cytometry, or fluorescence-activated cell sorting.

iv) The invention may be used to induce the formation of particle chains in the direction normal to the plane of the electrode. The chains represent conduits for current transport between the electrodes and their formation may reflect a field-induced polarization. Chains are much less mobile in transverse flow than are individual particles so that this effect may be used to separate particles according to the surface properties that contribute to the net polarization. The effect of reversible chain formation has been demonstrated under the experimental conditions stated herein. For example, the reversible formation of chains occurs, for carboxylated polystyrene beads of 1 micron diameter, at a voltage of 15 V (pp) at frequencies in excess of 1 MHz.

v) The invention may be used to isolate individual beads from a planar array.

Fluorescence binding assays in a planar array format, as described herein, may produce singular, bright beads within a large array, indicating particularly strong binding. To isolate and retrieve the corresponding beads, optical tweezers in the form of a sharply focused laser spot, may be employed to lock onto an individual bead of interest. The light-control component of the present invention may be used in conjunction with the optical tweezers to retrieve such an individual bead by moving the array relative to the bead, or vice versa, or by disassembling the array and retaining only the marked bead. This is a rather unique capability that will be particularly useful in the context of isolating beads in certain binding assays.

Commercial instrumentation is available to position optical tweezers in the field of a microscope. Larger scale motion is facilitated by translocating the array in-situ or simply by moving the external sample fixture. This process lends itself to automation in conjunction with the use of peak-finding image analysis software and feedback control.

vi) The invention may be used to implement a light-induced array sectioning ("shearing") operation to separate fluorescent, or otherwise delineated portions of an array from the remainder. This operation makes it possible to segment a given array and to isolate the corresponding beads for downstream analysis.

The basis for the implementation of this array segmentation is the light-control component of the present invention, in the mode of driving particles from an area of a Si/SiOx interface that is illuminated with high intensity. It is emphasized here that this effect is completely unrelated to the light-induced force on beads that underlies the action of optical tweezers. The present effect which operates on large sets of particles, was demonstrated under the experimental conditions stated herein using a 100 W illuminator on a Zeiss UEM microscope operated in epi-illumination. A simple implementation is to superimpose, on the uniform illumination pattern applied to the entire array, a line-focussed beam that is positioned by manipulation of beam steering elements external to the microscope. Beads are driven out of the illuminated linear portion. Other implementations take advantage of two separately controlled beams that are partially superimposed. The linear sectioning can be repeated in different relative orientations of shear and array.

EXAMPLE V

Fabrication of Spatially Encoded Bead Arrays

The present invention provides a method to transfer suspensions of beads or biomolecules to the electrode surface in such a way as to preserve the spatial encoding in the original arrangement of reservoirs, most commonly the conventional 8×12 arrangement of wells in a microtiter plate. Such a fluid transfer scheme is of significant practical importance given that compound libraries are commonly handled and shipped in 8×12 (or equivalent) wells.

The present invention utilizes chemical patterning to define individual compartments for each of M×N sets of beads and confine them accordingly. In the present instance, patterning is achieved by UV-mediated photochemical oxidation of a monolayer of thiol-terminated alkylsilane that is chemisorbed to the Si/SiOx substrate. Partial oxidation of thiol moieties produces sulfonate moieties and renders the exposed surface charged and hydrophilic. The hydrophilic portions of the surface, in the form of a grid of squares or circles, will serve as holding areas.

In accordance with the present invention, the first function of surface-chemical patterning into hydrophilic sections surrounded by hydrophobic portions is to ensure that droplets, dispensed from different wells, will not fuse once they are in contact with the substrate. Consequently, respective bead suspensions will remain spatially isolated and preserve the lay-out of the original M×N well plate. The second role of the surface chemical patterning of the present invention is to impose a surface charge distribution, in the form of the M×N grid pattern, which ensures that individual bead arrays will remain confined to their respective holding areas even as the liquid phase becomes contiguous.

Figure 6A:
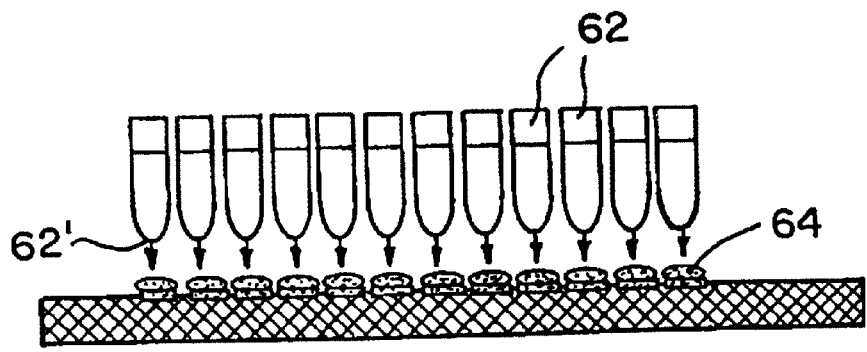
FIGS. 6a–c are side view illustrations of a layout-preserving transfer process from a microtiter plate to a planar cell.
Figure 6B:
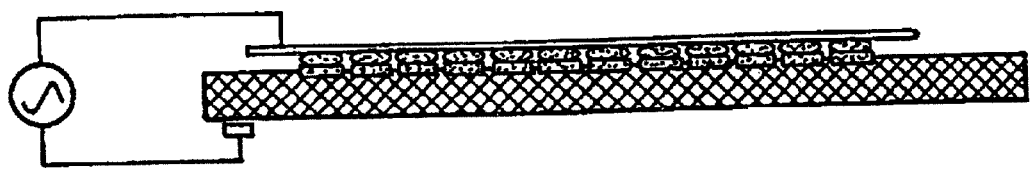
Figure 6C:
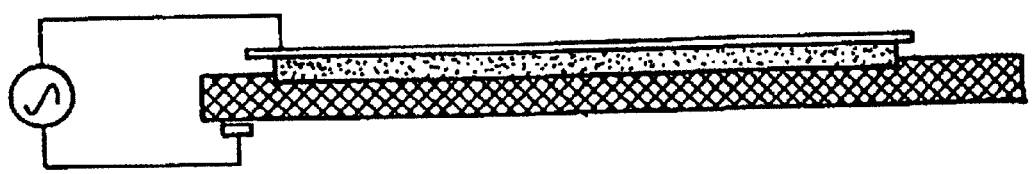

The layout-preserving transfer procedure involves the steps illustrated in FIGS. 6a–c. First, as shown in side view in FIG. 6a, the M×N plate of wells 62 is registered with the pattern 64 on the planar substrate surface. Well bottoms 62, are pierced to allow for the formation of pendant drops of suspension or, preferably, the process is facilitated by a fixture (not shown) providing M×N effective funnels to match the geometric dimensions of the M×N plate on the top and reduce the size of the dispensing end. Such a dispensing fixture will also ensure the precise control of droplet volumes, adjusted so as to slightly overfill the target holding area on the patterned substrate surface. The set of M×N drops is then deposited by bringing them in contact with the hydrophilic holding areas of the pre-patterned substrate and relying on capillary action.

Next, the plate is retracted, and the top electrode is carefully lowered to form the electrochemical cell, first making contact as shown in FIG. 6b, with individual liquid-filled holding areas on the substrate to which suspensions are confined. Overfilling ensures that contact is made with individual suspensions. The electric field is now turned on to induce array formation in the M×N holding areas and to ensure the preservation of the overall configuration of the M×N sets of beads while the gap is closed further (or filled with additional buffer) to eventually fuse individual droplets of suspension into a contiguous liquid phase as shown in FIG. 6c. In the fully assembled cell of FIG. 6c, while the droplets are fused together, the beads from each droplet are maintained in and isolated in their respective positions, reflecting the original M×N arrangement of wells. The present invention thus provides for the operations required in this implementation of a layout-preserving transfer procedure to load planar electrochemical cells.

EXAMPLE VI

Fabrication of Dynamic Planar Bead Arrays for Parallel Assays

The present invention provides a method to produce a heterogeneous panel of beads and potentially of biomolecules for presentation to analytes in an adjacent liquid. A heterogeneous panel contains particles or biomolecules which differ in the nature of the chemical or biochemical binding sites they offer to analytes in solution. The present method relies on the functional elements of the invention to assemble a planar array of a multi-component mixture of beads which carry chemical labels in the form of tag molecules and may be so identified subsequent to performing the assay. In the event of binding, the analyte is identified by examination of the bead, or cluster of beads, scoring positive.

Diagnostic assays are frequently implemented in a planar format of a heterogeneous panel, composed of simple ligands, proteins and other biomolecular targets. For example, in a diagnostic test kit, a heterogeneous panel facilitates the rapid testing of a given analyte, added in solution, against an entire set of targets. Heterogeneous panels of proteins are of great current interest in connection with the emerging field of proteome research. The objective of this research is to identify, by scanning the panel with sensitive analytical techniques such as mass spectrometry, each protein in a multi-component mixture extracted from a cell and separated by two-dimensional gel electrophotesis. Ideally, the location of each spot uniquely corresponds to one particular protein. This analysis would permit, for example, the direct monitoring of gene expression levels in a cell during a particular point in its cycle or at a given stage during embryonic development.

The fabrication of an array of heterogeneous targets is central to recently proposed strategies of drug screening and DNA mutation analysis in a planar format. The placement of ligands in a specific configuration on the surface of a planar substrate serves to maintain a key to the identity of any one in a large set of targets presented simultaneously to an analyte in solution for binding or hybridization. In an assay relying on fluorescence, binding to a specific target will create bright spots on the substrate whose spatial coordinates directly indicate the identity of the target.

Three principal strategies have been previously employed to fabricate heterogeneous panels. First, protein panels may be created by two-dimensional gel electrophoresis, relying on a DC electric field to separate proteins first by charge and then by size (or molecular weight). Even after many years of refinement, this technique yields results of poor reproducibility which are generally attributed to the poorly defined properties of the gel matrix.

Second, individual droplets, drawn from a set of reservoirs containing solutions of the different targets, may be dispensed either by hand or by employing one of several methods of automated dispensing (or "printing"; see e.g., Schena et al., Science 270, 467–470 (1995), the contents of which are incorporated herein by reference). Printing has been applied to create panels of oligonucleotides intended for screening assays based on hybridization. Printing leaves a dried sample and may thus not be suitable for proteins that would denature under such conditions. In addition, the attendant fluid handling problems inherent in maintaining, and drawing samples from a large number of reservoirs are formidable.

Third, target ligands may be created by invoking a variant of solid phase synthesis based on a combinatorial strategy of photochemically activated elongation reactions. This approach has been limited by very formidable technical problems in the chemical synthesis of even the simplest, linear oligomers. The synthesis of non-linear compounds in this planar geometry is extremely difficult.

The present invention of forming heterogeneous panels requires the chemical attachment of target ligands to beads. Ligands may be coupled to beads "off-line" by a variety of well established coupling reactions. For present purposes, the bead identity must be chemically encoded so it may be determined as needed. Several methods of encoding, including binary encoding, of beads are available. For example, short oligonucleotides may serve the purpose of identifying a bead via their sequence which may be determined by microscale sequencing techniques. Alternatively, chemically inert molecular tags may be employed that are readily identified by standard analytical techniques.

In contrast to all prior art methods, the present invention provides a novel method to create heterogeneous panels by in-situ, reversible formation of a planar array of chemically encoded beads in solution adjacent to an electrode. The array may be random with respect to chemical identity but is spatially ordered. This procedure offers several advantages. First, it is reversible so that the panel may be disassembled following the binding assay to discard beads scoring negative. Positive beads may be subjected to additional analysis without the need for intermediate steps of sample retrieval, purification or transfer between containers. Second, the panel is formed when needed, that is, either prior to performing the actual binding assay, or subsequent to performing the assay on the surface of individual beads in suspension. The latter mode minimizes potential adverse effects that can arise when probes bind to planar target surfaces with a high concentration of target sites. Third, to accommodate optical analysis of individual beads, interparticle distances within the array may be adjusted by field-induced polarization or by the addition of inert spacer particles that differ in size from the encoded beads. FIG. 7 shows the use of small spacer beads 72 for separating encoded beads 74. As shown, the spacing of beads 74 is greater than the spacing of comparable beads in FIG. 4b. Finally, UV-mediated oxide regrowth, as provided by the present invention, readily facilitates the embedding of a grid pattern of selected dimension into the substrate to ensure the formation of small, layout-preserving subarrays in the low-impedance fields of the grid.

To create the panel, a multi-component mixture of beads carrying, for example, compounds produced by bead-based combinatorial chemistry, is placed between electrodes. Each type of bead may be present in multiple copies. Arrays are formed in response to an external field in a designated area of the electrode surface. This novel approach of in-situ assembly of panels relies on beads that carry a unique chemical label, or code, to permit their identification subsequent to the completion of a binding assay. Alternatively, beads may be marked ("painted") on-line by way of a photochemical bead-coloring method. Selected beads in an array are individually illuminated by a focused light source to trigger a coloring reaction on the bead surface or in the bead interior to indicate a positive assay score. Beads so marked can be subsequently separated from unmarked beads by a light-activated sorting method described herein. Numerous UV-activated reactions are available to implement this bead-coloring method.

The present invention provides for several methods of discarding beads with negative scores, typically the vast majority, while retaining those with positive scores. This method take advantage of the fact that, in contrast to all prior art methods, the array represents a temporary configuration of particles that is maintained by the applied electric field and may be rearranged or disassembled at will. This capability, along with the fact that biomolecules are never exposed to air (as in the prior art method of printing) facilitates the in-situ concatenation of analytical procedures that require the heterogeneous panel in conjunction with subsequent, "downstream" analysis.

First, if positive beads are clustered in a subsection of the array, the light-controlled array splitting operation of the present invention may be invoked to dissect the array so as to discard negative portions of the array (or recycle them for subsequent use). Second, if positive and negative beads are randomly interspersed, a fluorescence-activated sorting method, implemented on the basis of the present invention in a planar format, as described herein, may be invoked. In the case of fluorescence-activated sorting, positive and negative beads may be identified as bright and dark objects, respectively. In the special case that only a few positive beads stand out, these may be removed from the array by locking onto them with optical tweezers, a tool to trap and/or manipulate individual refractive particles under illumination, and disassembling the array by removing the field, or subjecting the entire array to lateral displacement by the fundamental operations of the present invention.

The typical task in screening a large set of compounds is one of looking for a very small number of positive events in a vast number of tests. The set of discarded beads will typically involve the majority at each stage in the assay. The procedure of the present invention therefore minimizes the effort invested in negative events, such as the challenging in-situ synthesis of target ligands irrespective of whether or not they will prove to be of interest by binding a probe offered in solution.

The method of forming a heterogeneous panel according to the present invention contains beads of each type in generally random assembly. The creation of a heterogeneous panel with each position in the panel containing a cluster of beads of the same type, that is, beads originating in the same reservoir (FIG. 6a), may be desirable so as to ensure a sufficiently large number of positive events to facilitate detection. A practical solution follows from the application of the layout-preserving fluidic transfer scheme described herein. In this procedure, beads from an M×N well plate are transferred layout-preservingly onto a chemically patterned substrate in such a way as to preserve the spatial encoding of bead identities.

EXAMPLE VII

Binding and Functional Assays in Planar Bead Array Format

The present invention can be used to implement mixed-phase binding assays as well as certain functional assays in a planar array format. Several combinations are possible reflecting the presence of probe or target in solution, on the surface of colloidal beads, or on the electrode surface. The methods of the present invention facilitate the formation of a planar array to present targets to probes in solution prior to performing the binding assay ("pre-formed" array; FIG. 8). Alternatively, a planar array of beads may be formed in front of a detector surface subsequent to performing the binding assay in suspension ("post-formed" array; FIG. 8). The present invention also provides the methods to implement functional assays by enabling the assembly of certain cell types adjacent to a planar detector or sensor surface to monitor the effects of exposure of the cells to small molecule drugs in solution.

Binding assays, particularly those involving proteins such as enzymes and antibodies, represent a principal tool of medical diagnostics. They are based on the specific biochemical interaction between a probe, such as a small molecule, and a target, such as a protein. Assays facilitate the rapid detection of small quantities of an analyte in solution with high molecular specificity. Many procedures have been designed to produce signals to indicate binding, either yielding a qualitative answer (binding or no binding) or quantitative results in the form of binding or association constants. For example, when an enzyme binds an analyte, the resulting catalytic reaction may be used to generate a simple color change to indicate binding, or it may be coupled to other processes to produce chemical or electrical signals from which binding constants are determined. Monoclonal antibodies, raised from a single common precursor, may be prepared to recognize virtually any given target, and immunoassays, based on antibody-antigen recognition and binding, have developed into an important diagnostic tool. As with enzyme binding, antibody binding of an antigenic analyte may be detected by a variety of techniques including the classic method of enzyme-linked immunoassays (ELISA) in which the reaction of an antibody-coupled enzyme is exploited as an indicator. A common and conceptually simple scheme ensures the detection of antibody binding to a target analyte by supplying a fluorescently labeled second antibody that recognizes the first (or primary) antibody.

Binding assays involving soluble globular proteins are often performed in solution to ensure unbiased interactions between protein and target. Such liquid phase assays, especially when performed at low concentrations of target or probe, minimize potential difficulties that may arise when either target or probe are present in abundance or in close proximity. By the same token, the kinetics tend to be slow. Cooperative effects, such as crowding, arising from the close proximity of probes must be carefully controlled when either probe or target is chemically anchored to a solid substrate.

Nonetheless, this latter solid phase format of binding assays is also very commonly employed whenever the situation demands it. For example, the presence of a protein on the surface of a cell may be exploited in "panning" for the cells that express this protein in the presence of many other cells in a culture that do not: desired cells attach themselves to the surface of a container that is pre-coated with a layer of a secondary antibody directed against a primary antibody decorating the desired cell-surface protein. Similarly, certain phages may be genetically manipulated to display proteins on their surface, and these may be identified by a binding assay involving a small molecule probe such as an antigen if the protein displayed is an antibody (Watson et al., "Recombinant DNA", 2nd Edition (Scientific American Books, W. H. Freeman and Co., New York, N.Y., 1983), the contents of which are incorporated herein by reference). In addition, the planar geometry accommodates a variety of optical and electrical detection schemes implemented in transducers and sensors.

A combination of liquid phase and solid phase assay may be developed by using beads that are decorated with either probe or target, as in procedures that employ decorated magnetic beads for sample preparation or purification by isolating binding from non-binding molecules in a given multi-component mixture. Recent examples of the use of these beads include the purification of templates for DNA sequencing applications or the extraction of Mona from (lysed) cells by hybridization to beads that are decorated with poly-adenine (polyA) residues.

Functional assays involving suitable types of cells are employed to monitor extracellular effects of small molecule drugs on cell metabolism. Cells are placed in the immediate vicinity of a planar sensor to maximize the local concentration of agents released by the cell or to monitor the local pH.

The present invention provides the means to implement mixed phase binding assays in a planar geometry with a degree of flexibility and control that is not available by prior art methods. Thus, it offers the flexibility of forming, in-situ, reversibly and under external spatial control, either a planar panel of target sites for binding of analyte present in an adjacent liquid phase, or a planar array of probe-target complexes subsequent to performing a binding assay in solution. Binding may take place at the surface of individual beads suspended in solution, at the surface of beads pre-assembled into arrays adjacent to the electrode surface, or at the electrode surface itself. Either the target or probe molecule must be located on a bead to allow for a bead-based assay according to the present invention. As shown in FIG. 8, if the probe molecule P is located on a bead, then the target molecule T may be either in solution, on a bead or on the electrode surface. The converse is also true.

For example, the methods of the present invention may be used to implement panning, practiced to clone cell surface receptors, in a far more expeditious and controlled manner than is possible by the prior art method. Given a substrate that has been coated with a layer of antibody directed against the sought-after cell surface protein, the present invention facilitates the rapid assembly of a planar array of cells or decorated beads in proximity to the layer of antibodies and the subsequent disassembly of the array to leave behind only those cells or beads capable of forming a complex with the surface-bound antibody.

A further example of interest in this category pertains to phage displays. This technique may be employed to present a layer of protein targets to bead-anchored probes. Bead arrays may now be employed to identify a protein of interest. That is, beads are decorated with small molecule probes and an array is formed adjacent to the phage display. Binding will result in a probe-target complex that retains beads while others are removed when the electric field is turned off, or when light-control is applied to remove beads from the phage display. If beads are encoded, many binding tests may be carried out in parallel because retained beads may be individually identified subsequent to binding.

The methods of the present invention readily facilitate competitive binding assays. For example, subsequent to binding of a fluorescent probe to a target-decorated bead in solution and the formation of a planar bead array adjacent to the electrode, fluorescent areas within the array indicate the position of positive targets, and these may be further probed by subjecting them to competitive binding. That is, while monitoring the fluorescence of a selected section of the planar array, an inhibitor (for enzyme assays) or other antagonist (of known binding constant) is added to the electrochemical cell, and the decrease in fluorescence originating from the region of interest is measured as a function of antagonist concentration to determine a binding constant for the original probe. This is an example of a concatenation of analytical steps that is enabled by the methods of the present invention.

The fact that a probe-target complex is fixed to a colloidal bead, as in the methods of the present invention, conveys practical advantages because this facilitates separation of positive from negative events. Particularly when solid phase assays are performed on a planar substrate, an additional advantage of planar bead arrays is the enhancement of light collection efficiency provided by the beads, as discussed herein.

If desired, beads may serve strictly as delivery vehicles for small molecule probes. That is, an array of probe-decorated beads is formed adjacent to a target-decorated surface in accordance with the methods of the present invention. UV-activated cleavage of the probe from the bead support will ensure that the probe is released in close proximity to the target layer, thereby enhancing speed and efficiency of the assay. The identity of the particular probe interacting with the target may be ascertained from the positional location of the bead delivering the probe.

The methods of the present invention apply not only to colloidal beads of a wide variety (that need no special preparative procedures to make them magnetic, for example), but also to lipid vesicles and cells that are decorated with, or contain embedded in their outer wall, either probe or target. The methods of the present invention may therefore be applied not only to bead-anchored soluble proteins but potentially to integral membrane receptors or to cell surface receptors.

In particular, the rapid assembly of cells in a designated area of the substrate surface facilitates the implementation of highly parallel cell-based functional assays. The present invention makes it possible to expose cells to small molecule drug candidates in solution and rapidly assemble them in the vicinity of a sensor embedded in the electrode surface, or to expose pre-assembled cells to such agents that are released into the adjacent liquid phase. In the simplest case, all cells will be of the same type, and agents will be administered sequentially. Even in this sequential version, electrokinetic mixing will enhance through-put. However, as described herein, the methods of the present invention also enable the parallel version of binding assays and thus of functional assays in a planar format by encoding the identity of different cells by a "Layout-Preserving Transfer" process from an 8×12 well plate, as discussed herein, and to isolate cells scoring positive by providing feed-back from a spatially resolved imaging or sensing process to target a specific location in the array of cells.

EXAMPLE VIII

Screening for Drug Discovery in Planar Geometry

The functional elements of the present invention may be combined to implement procedures for handling and screening of compound and combinatorial libraries in a planar format. The principal requisite elements of this task are: sample and reagent delivery from the set of original sample reservoirs, commonly in a format of 8×12 wells in a microtiter plate, into a planar cell; fabrication of planar arrays of targets or of probe-target complexes adjacent to the planar electrode surface prior to or subsequent to performing a binding assay; evaluation of the binding assay by imaging the spatial distribution of marker fluorescence or radioactivity, optionally followed by quantitative pharmacokinetic measurements of affinity or binding constants; isolation of beads scoring positive, and removal from further processing of other beads; and collection of specific beads for additional downstream analysis. The present invention relates to all of these elements, and the fundamental operations of the invention provide the means to concatenate these procedures in a planar format.

A central issue in the implementation of cost-effective strategies for modern therapeutic drug discovery is the design and implementation of screening assays in a manner facilitating high throughput while providing pharmacokinetic data as a basis to select promising drug leads from a typically vast library of compounds. That is, molecular specificity for the target, characterized by a binding constant, is an important factor in the evaluation of a new compound as a potential therapeutic agent. Common targets include enzymes and receptors as well as nucleic acid ligands displaying characteristic secondary structure.

The emerging paradigm for lead discovery in pharmaceutical and related industries such as agricultural biotechnology, is the assembly of novel synthetic compound libraries by a broad variety of new methods of solid state "combinatorial" synthesis. Combinatorial chemistry refers to a category of strategies for the parallel synthesis and testing of multiple compounds or compound mixtures in solution or on solid supports. For example, a combinatorial synthesis of a linear oligopeptide containing n amino acids would simultaneously create all compounds representing the possible sequence permutations of n amino acids. The most commonly employed implementation of combinatorial synthesis relies on colloidal bead supports to encode reaction steps and thus the identity of each compound. Beads preferred in current practice tend to be large (up to 500 microns in diameter) and porous to maximize their compound storage capacity, and they must be encoded to preserve the identity of the compound they carry.

Several methods of encoding, or binary encoding, of beads are available. Two examples are as follows. First, beads may be labeled with short oligonucleotides such as the 17-mers typically employed in hybridization experiments. The sequence of such short probes may be determined by microscale sequencing techniques such as direct Maxam-Gilbert sequencing or mass spectrometry. This encoding scheme is suitable when the task calls for screening of libraries of nucleic acid ligands or oligopeptides. Second, members of a combinatorial library may be associated with chemically inert molecular tags. In contrast to the previous case, these tag molecules are not sequentially linked. Instead, the sequence of reaction steps is encoded by the formal assignment of a binary code to individual tag molecules and their mixtures that are attached to the bead in each successive reaction step. The tags are readily identified by standard analytical techniques such as gas chromatography. This general encoding strategy is currently employed in the synthesis of combinatorial libraries on colloidal beads.

Commercial compound libraries are large, given that even for the aforementioned 17-mer, the number of sequence permutations is $4^{17}$, or approximately $^{\sim}10$. However, the high specificity of typical biological substrate-target interactions implies that the vast majority of compounds in the collection will be inactive for any one particular target. The task of screening is to select from this large set the few potential lead compounds displaying activity in binding or in functional assays. The principal drug discovery strategy widely applied to natural compound libraries in the pharmaceutical industry is to select individual compounds from the library at random and subject them to a series of tests. Systematic screening procedures are thus required to implement the rapid screening and scoring of an entire library of synthetic compounds, in practice often containing on the order of $10^{7}$ items.

In current practice, compounds are first cleaved and eluted from their solid supports and are stored in microtiter plates. Further sample handling in the course of screening relies primarily on robotic pipetting and transfer between different containers, typically wells in microtiter plates. While robotic workstations represent a step in the direction of automating the process, they rely on the traditional format of microtiter plates containing 8×12 wells and sample handling by pipetting and thus represent merely an incremental operational improvement. A significant additional consideration is the need to conserve reagent and sample by reducing the spatial scale of the analytical procedures.

The present invention provides a set of operations to realize integrated sample handling and screening procedures for bead-based compound libraries in a planar format. This will significantly reduce time and cost due to reagent and sample volumes. The principal advantage of the methods of the present invention is that they provide a large set of fundamental operations to manipulate sets of beads in a planar format, permitting the handling of beads between stations in a multi-step analytical procedure.

In particular, as previously described herein, the methods of the present invention facilitate the implementation of the following pertinent procedures: transfer of samples from microtiter plates to a planar electrochemical cell; formation of heterogeneous panels of target sites adjacent to the substrate surface; solid phase binding assays; and isolation of specific beads from an array. In addition, the fundamental operations of the present invention provide the means to concatenate these procedures on the surface of a planar electrode.

As described herein for hybridization assays, several variants are possible. That is, binding assays may be performed by allowing protein targets such as enzymes to bind to compounds on the surface of a bead, either in suspension or arranged in a planar array. The common practice of combinatorial chemistry based on large porous carrier beads accommodates the concurrent handling of smaller beads to whose outer surface compounds are anchored via inert chemical spacers. Such small beads (up to 10 microns in diameter) are readily manipulated by the methods of the present invention. Large beads are used as labeled compound storage containers.

Alternatively, binding between target and a radioactively or otherwise labeled probe may occur in solution, within microtiter plate wells, if compounds have already been cleaved from their synthesis support. In that case, probe-target complexes may be captured by complexation to encoded beads in each well, for example via the secondary antibody method of coupling the protein target to a bead-anchored antibody. Bead-captured probe-target complexes are then transferred to the planar cell for proximity analysis and further processing as illustrated in FIG. 10. As shown in FIG. 10, probe-target complexes 102 are allowed to form in solution. Antibody coated beads 104 are added to the solution, resulting in a bead anchored complex 106. The bead anchored complexes 106 are deposited onto electrode 108 from wells 110, and a planar array of bead anchored complexes is formed. When fluorescent probes 114 are used, these impart fluorescence to the bead anchored complex, facilitating detection.

The methods and apparatus of the present invention are well suited to the task of identifying a small number of positive events in a large set. The imaging of an entire array of probe-target complexes is further enhanced by proximity to an area detector, and by bead lensing action. The isolation of a small number of positive scores from the array is readily achieved, for example by applying optical tweezers, as described herein. The large remainder of the array may then be discarded. This in turn considerably reduces the complexity of applying more stringent tests, such as the determination of binding constants, because these may be restricted to the few retained beads. These tests may be directly applied, without the need for additional sample transfer to new containers, to the samples surviving the first screening pass.

EXAMPLE IX

Hybridization Assays in Planar Array Format

The present invention can be used to implement solid phase hybridization assays in a planar array format in a configuration related to that of a protein binding assay in which target molecules are chemically attached to colloidal beads. The methods of the present invention facilitate the formation of a planar array of different target oligonucleotides for presentation to a mixture of strands in solution. Alternatively, the array may be formed subsequent to hybridization in solution to facilitate detection and analysis of the spatial distribution of fluorescence or radioactivity in the array.

Considerable research and development is presently being invested in an effort to develop miniaturized instrumentation for DNA sample extraction and preparation including amplification, transcription, labeling and fragmentation, with subsequent analysis based on hybridization assays as well as electrophoretic separation. Hybridization assays in planar array format are being developed as a diagnostic tool for the rapid detection of specific single base pair mutations in a known segment of DNA, and for the determination of expression levels of cellular genes via analysis of the levels of corresponding mRNAs or cDNAs. Hybridization of two complementary single strands of DNA involves molecular recognition and subsequent hydrogen bond formation between corresponding nucleobases in the two opposing strands according to the rules A-T and G-C; here A, T, G and C respectively represent the four nucleobases Adenine, Thymine, Guanosine and Cytosine found in DNA; in RNA, Thymine is replaced by Uracil. The formation of double-strand, or duplex, DNA requires the pairing of two highly negatively charged strands of DNA, and the ionic strength of the buffer, along with temperature, plays a decisive role.

As previously discussed herein, two principal methods to prepare heterogeneous arrays of target strands on the surface of a planar substrate are micro-dispensing ("printing") and in-situ, spatially encoded synthesis of oligonucleotides representing all possible sequence permutations for a given total length of strand. In this context, hybridization must necessarily occur in close proximity to a planar substrate surface and this condition requires care if complications from steric hindrance and from non-specific binding of strands to the substrate are to be avoided. Non-specific adsorption can be a serious problem, especially in the presence of DC electric fields employed in current commercial designs that rely on electrophoretic deposition to accelerate the kinetics of hybridization on the surface. In addition, there are the technical difficulties, previously discussed herein, resulting from steric hindrance and from collective effects reflecting the crowding of probe strands near the surface.

In the context of DNA analysis, colloidal (magnetic) beads are commonly used. For example, they are employed to capture DNA in a widely used screening procedure to select cDNAs from clone libraries. Specifically, cDNAs are allowed to hybridize to sequences within long genomic DNA that is subsequently anchored to magnetic beads to extract the hybridized cDNA from the mixture.

The present invention facilitates the formation of planar arrays of oligonucleotide-decorated colloidal beads, either prior to or subsequent to hybridization of a fluorescence probe strand to the bead-anchored target strand or subsequent to hybridization in free solution and bead capture of the end-functionalized target strand. In contrast to prior art methods, the present invention does not require hybridization to occur in the vicinity of planar substrate surface, although this is an option if bead-anchored probe strands are to be delivered to substrate-anchored target strands.

The ability to perform hybridization either in solution, on the surface of individual beads, or at the substrate surface provides an unprecedented degree of flexibility. In addition, the advantages of bead arrays, as described herein, make it feasible to select and isolate individual beads, or groups of beads, from a larger array on the basis of the score in a hybridization assay. This isolation facilitates the implementation of subsequent assays on the strands of interest. The fact that beads remain mobile also means that beads of interest may be collected in designated holding areas for micro-sequencing, or may be moved to an area of substrate designated for PCR amplification.

The methods of the present invention may be used to implement a hybridization assay in a planar array format in one of two principal variations. All involve the presence of the entire repertoire of beads in the planar array or panel formed adjacent to the electrode surface for parallel read-out. As with heterogeneous panels in general, the arrangement of beads within the array is either random (with respect to chemical identity), and the identity of beads scoring high in the binding assay must be determined subsequently, or it is spatially encoded by invoking the "Layout-Preserving Transfer" method of sample loading described herein.

The former variant is readily implemented and accommodates array formation either prior to or subsequent to performing the binding assay. For example, binding may be performed in suspension before beads are assembled into the array. As with the aforementioned cDNA selection procedure, the method of the present invention also accommodates the use of beads as capture elements for end-functionalized target DNA, for example, via biotin-streptavidin complexation. In this latter case, beads serve as a delivery vehicle to collect all probe-target complexes to the electrode surface where they are assembled into an array for ease of analysis. In particular, proximity CCD detection of beads on electrodes will benefit from the lensing action of the beads in the array. This version of the assay is preferably used if only a small number of positive scores are expected.

Hybridization to a pre-formed bead array can take advantage of a variant of the assay which preserves spatial encoding. An array of bead clusters is formed by the "Layout-Preserving Transfer" method previously described herein, and exposed to a mixture of cDNAs. The resulting spatial distribution of fluorescence intensity or radioactivity reflects the relative abundance of cDNAs in the mixture. This procedure relies on the detection of a characteristic fluorescence or other signal from the probe-target complex on the surface of a single bead. Given the fact that the array is readily held stationary by the methods of the present invention, image acquisition may be extended to attain robust signal-to-noise for detection of low level signals. For example, a signal generated by a bead of 10 micron diameter with at most $10^8$ probe-target complexes on the surface of the bead may be detected. Bead lensing action also aids in detection.

As with the implementation of drug screening, the functional elements of the present invention may be combined to perform multiple preparative and analytical procedures on DNA.

EXAMPLE X

Alignment and Stretching of DNA in Electric Field-Induced Flow

The present invention can be used to position high-molecular weight DNA in its coiled configuration by invoking the fundamental operations as they apply to other colloidal particles. However, in addition, the electrokinetic flow induced by an electric field at a patterned electrode surface may be employed to stretch out the DNA into a linear configuration in the direction of the flow.

Procedures have been recently introduced which rely on optical imaging to construct a map of cleavage sites for restriction enzymes along the contour of an elongated DNA molecule. This is generally known as a "restriction map". These procedures, which facilitate the study of the interaction of these and other proteins with DNA and may also lead to the development of techniques of DNA sequencing, depend on the ability to stretch and align DNA on a planar substrate.

For individual DNA molecules, this has been previously achieved by subjecting the molecule to elongational forces such as those exerted by fluid flow, magnetic fields acting on DNA-anchored magnetic beads or capillary forces. For example, DNA "combs" have been produced by simply placing DNA molecules into an evaporating droplet of electrolyte. If provisions are made to promote the chemical attachment of one end of the molecule to the surface, the DNA chain is stretched out as the receding line of contact between the shrinking droplet and the surface passes over the tethered molecules. This leaves behind dry DNA molecules that are attached in random positions within the substrate area initially covered by the droplet, stretched out to varying degrees and generally aligned in a pattern of radial symmetry reflecting the droplet shape. Linear "brushes", composed of a set of DNA molecules chemically tethered by one end to a common line of anchoring points, have also been previously made by aligning and stretching DNA molecules by dielectrophoresis in AC electric fields applied between two metal electrodes previously evaporated onto the substrate.

The present invention invokes electrokinetic flow adjacent to an electrode patterned by UV-mediated regrowth of oxide to provide a novel approach to the placement of DNA molecules in a predetermined arrangement on a planar electrode surface, and to the stretching of the molecules from their native coil configuration into a stretched, linear configuration that is aligned in a pre-determined direction. This process is shown in FIG. 11 and is accomplished by creating controlled gradients in the flow vicinity across the dimension of the DNA coil. The velocity gradient causes different portions of the coil to move at different velocities thereby stretching out the coil. By maintaining a stagnation point at zero velocity, the stretched coil will be fixed in position. This method has several advantages over the prior art approaches. First, DNA molecules in their coiled state are subjected to light control to form arrays of desired shape in any position on the surface. This is possible because large DNA from cosmids or YACs forms coils with a radius in the range of one micron, and thus acts in a manner analogous to colloidal beads. A set of DNA molecules may thus be steered into a desired initial arrangement. Second, UV-patterning ensures that the elongational force created by the electrokinetic flow is directed in a predetermined direction. The presence of metal electrodes in contact with the sample, a disadvantage of the dielectrophoretic prior art method, is avoided by eliminating this source of contamination that is difficult to control especially in the presence of an electric field. On patterned Si/SiOx electrodes, flow velocities in the range of several microns/second have been generated, as required for the elongation of single DNA molecules in flow. Thus, gradients in the flow field determines both the fractional elongation and the orientation of the emerging linear configuration. Third, the present invention facilitates direct, real-time control of the velocity of the electric field-induced flow, and this in turn conveys explicit control over the fractional elongation.

This invention is also for a method and apparatus to direct the lateral motion and induce the assembly into planar arrays of cells on semiconductor surfaces in response to temporally and spatially varying electric fields and to projected patterns of illumination.

The response of different types of cells to variations in the frequency and voltage of the applied electric field and to specific patterns and changing intensity of illumination enables the on-cue assembly of multiple arrays of cells in any desired position on the substrate, and further enables the repositioning, disassembly and re-assembly and more generally the reconfiguration and segmentation of such arrays. Time-constant and time-varying illumination patterns are generated by an optically programmable illumination pattern generator may be used and can be based on a graphical representation of the pattern created on a personal computer.

The novel methodology of image cytometry introduced in the present invention relates to the general fields of molecular and cellular biology and has applications in the fields of diagnostics, genetic analysis, cell biology and drug discovery. The image cytometry facilitates a multiplicity of cell-based biological and biochemical procedures based on the quantitative analysis of images recorded from array of cells. As with Random Encoded Array Detection (READ) or Programmable Array Reconfiguration and Segmentation (PARSE), these assays are performed in a highly parallel format in a small volume of sample on the surface of a semiconductor wafer.

The novel method of image cytometry according to the present invention may be used in a number of different applications, including:

cell-typing analysis based on the decoration of cell-surface markers with tagged probes such as fluorescence labeled antibodies or antibodies that are coupled to flourescent beads. Specific applications include bacterial strain typing; HLA typing (transplantation donor-recipient matching); immunophenotyping;

diagnostic assays based on the identification of cell types and quantitative evaluation of relative counts of different cell types in a given sample, for example, the determination of the fraction of CD-4 cells in a population to assess levels of HIV infection;

on-chip fractionation of a mixture of cells into sub-populations based on:

selective affinity of cell phenotypes using antibodies or lectin (Nordon et al, "An Experimental Model of Affinity Cell Separation", Cytometry 16, 25–33 (1994), the contents of which are incorporated herein by reference; see also: "panning" for clones expressing specific antibodies). Using beads displaying such antibodies or lectins, cross-linking between cells may be induced to form clusters that are readily distinguished and separated from individual cells;

differential mobility in response to time-varying or to time-constant but spatially varying (inhomogeneous) electric fields or to gradients in electrochemical environment created by LEAPS near an electrolyte-insulator-semiconductor (EIS) interface;

combinations with controlled flow configurations such as those in various realizations of field flow fractionation (for example, see: Bigelow et al, "Separation of B and T lymphocytes by a hybrid field-flow fractionation/adhesion chromatography technique", J. Immunological Methods 117, 289–293 (1989); Markx et al, "Dielectrophoretic characterization and separation of microorganisms", Microbiology 140, 585–591 (1994); Huang et al, "Introducing Dielectrophoresis as a New Force Field for Field Flow Fractionation", Biophysical J. 73, 1118–1129 (1997); the contents of all of which are incorporated herein by reference);

cell-based functional assays monitoring the levels of expressed cell-surface markers or the activation or regulation of pathways, such as signal transduction pathways and metabolic pathways. The expression of the surface markers may be detected by affinity binding between the markers and fluorescence or enzyme labeled probes. The endpoints of the pathways may be analyzed through intracellular fluorescent signal generated by enzymes such as luciferin (PE Corporation/Tropix) or β-lactamase (Aurora);

cell secretion-based analysis that could be used in drug and ligand screening;

cell-cell interactions revealed by adhesion markers on cell surfaces;

cytotoxicity assays based on the labeling of indicators such as phosphatidylserine which appears on the outer membrane of cells in the early stages of apoptosis; and chemotaxis analysis based on the tracking of cells positioned in controlled configurations in known spatial relation to gradients in the concentration of chemotactic agents.

The image cytometry according to the present invention permits the efficient realization of a wide variety of cell-based functional as well as diagnostic assays based on the analysis of multi-color fluorescence or other optical markers imaged on the surfaces of individual cells. In addition, the methodology also permits the separation and fractionation of multiple cell types in a mixture based on differential response to electro-optic stimuli as disclosed herein. Imaging and profiling applications may invoke a variation of the READ format while fractionation and sorting into multiple sub-populations may invoke the PARSE format.

The integration of this novel methodology of cellular analysis with sample preparation (electric-field induced lysis of cells) along with the technology of optically programmable bead arrays as disclosed herein creates a novel platform that combines an "on-chip"format of quantitative molecular interaction analysis and cellular analysis with microfluidics and optical imaging into a novel, multi-purpose assay platform.

Imaging of Cells

In its simple form, image cytometry is practiced in the doctor's office when blood or other liquid samples are spotted onto segmented glass slides and populations of cells are "manually" counted. These and related simple implementations of cellular analysis invoke the simple spotting of cells onto solid supports where cells settle under gravity, typically in random positions at low lateral density. However, even in this simple format, certain advantages of the approach have been recognized (Galbraith et al, "Imaging Cytometry by Multiparameter Fluorescence", Cytometry 12, 579–596 (1991), the contents of which are incorporated herein by reference): the power of image analysis can be brought to bear to facilitate the analysis of multi-color fluorescence images. A major drawback is the very low "throughput" of this approach, given the low density of cells which must be maintained to avoid the risk of forming three-dimensional clusters in which the view of some of the cells would be obstructed. A further drawback is that methods of cellular analysis invoking differential mobility of cells in response to external stimuli are not available.

Flow Cytometry

Flow cytometry and its application to fluorescence-activated cell sorting rely on a serial mode of analysis that requires the capture of individual cells into droplets which are passed, one at a time, through a small observation window. During a short time, e.g., 1–10 μs, all measurements on a given cell must be completed. For example, the simultaneous analysis of a small number of cell surface markers represents the state of the art in flow cytometry (Beavis and Pennline, "Detection of Cell-Surface Antigens Using Antibody-conjugated Fluorospheres", BioTechniques 21, 498–503 (1996), the contents of which are incorporated herein by reference). Flow cytometric analysis represents just the last step in an assay: the instrumentation does not lend itself to the integration of liquid handling and automation of bioanalytical assays. This is in significant contrast to the present invention which integrates the optical manipulation of bead arrays and cellular assembly technology with microfluidics and optical imaging into a miniaturized platform for quantitative molecular and cellular analysis.

Recent developments of smaller and more specialized instruments notwithstanding, the intrinsic complexity of flow cytometry requires specialized and expensive instrumentation including multiple laser sources of high power, matching detectors and fast electronics to handle the acquisition and processing of signals during the short available interrogation interval during which each cell traverses the detection window. Sorting requires additional steps and equipment. Even after many years of commercial development, the operation of flow cytometers requires trained personnel to handle calibration and ensure reliable performance. The cost of commercial instruments, for example, those offered by Becton-Dickinson, Beckman Coulter or Cytomation is prohibitive for all but major medical centers or research institutions.

Sorting and Separation of Cells by Affinity and/or Flow

Several realizations have been described for the fractionation of cells by selective affinity for, and hence differential retention by a nearby solid phase or by differential mobility in superimposed force fields such as a fluid flow with superimposed transverse electric field (field flow fractionation or FFF) or by combinations thereof. Differential dielectrophoretic levitation of cells above a set of interdigitated electrodes and fractionation in a transverse flow represents a recent addition to this set of techniques which offers the potential for differential blood cell analysis. As with other FFF techniques, the latter method relies on downstream detection of individual cells and thus resembles flow cytometry with respect to the implied serial processing to establish the identity of sub-populations. A further disadvantage is the requirement for an elongated channel to permit the spatial separation between sub-populations.

Cytometry According to the Present Invention

Cytometry according to the present invention subsumes the entire set of capabilities for cellular analysis illustrated above into a common platform which is miniaturized and integrated with microfluidics and optical imaging and compatible with quantitative bear array format of molecular interaction analysis whose capabilities may be used in "multiplexed" fluorescence immunoassays and DNA hybridization assays.

The specific advantages of the cytometry according to the present invention include:

high throughput resulting from the high densities of the cellular assemblies (for example, 10^4–10^6/mm^2) and the parallel mode of signal acquisition afforded by imaging;

integration of sample preparation, fluid handling and assay readout, for example, integration with on-chip assay formats;

parallel processing based on imaging of multiple colors and morphological parameters;

light-directed transport and assembly of cells;

light-guided separation and fractionation of cells into sub-populations based on optically programmable illumination patterns and frequency dispersion in the dielectrophoretic response; and significant reduction in expense of instrumentation.

The method and apparatus of the present invention enables the parallel processing of large numbers of cells assembled into dense planar assemblies; typically, 10^4 cells of 10 $\mu$m diameter will be accommodated in an area as small as 1 mm^2. Smaller bacterial cells such as *E. coli* can be accommodated in even higher density. In significant contrast to flow cytometry, signals are collected simultaneously from a large number of cells by way of imaging, and the rate of acquiring signal is very high even when cells are held stationary.

The present invention presents a very significant advantage, especially when multiple colors are to be discriminated and are to be quantitatively determined by analysis of multi-color images of individual cell surfaces. Thus, the cytometry according to the present invention will readily accommodate multiple cell surface markers and additional morphological indicators for individual cells (size, shape) or mutually interacting clusters of cells. This is generally possible even without specialized equipment. In fluorescence immunoassays using the READ bead array format, the capability has been demonstrated using an inexpensive consumer-grade video CCD camera, of detecting signals from individual beads displaying only 1000 labeled antibody molecules. Higher levels of sensitivity are possible for detection of markers on cell surfaces because fluorescent beads may be used as the label to decorate the cells.

A. Cells Form Arrays in Response to AC Electric Fields

Figure 12:
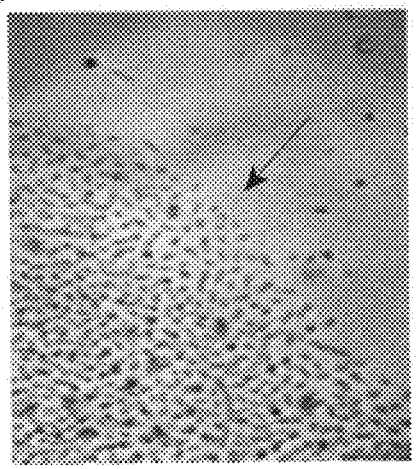
FIG. 12 is an illustration of E. coli cells (grown to log phase and suspended in 280 mM mannitol solution at the density of $10^8$/ml) which form arrays under electric field. (Bright field image. 25×obj, NA 0.45. Electric field: 5V, 200 Hz)

Referring now to FIG. 12, therein is illustrated *E. coli* cells (grown to log phase and suspended in 280 mM mannitol solution at the density of $10^8$/ml) which form arrays under electric field. On the left side of the field, the cells are assembled at very high density. Some singlet cells at the right side are moving to the left to join the array. (Bright field image. 25×obj, NA 0.45. Electric field: 5V, 200 Hz).

Figure 13:
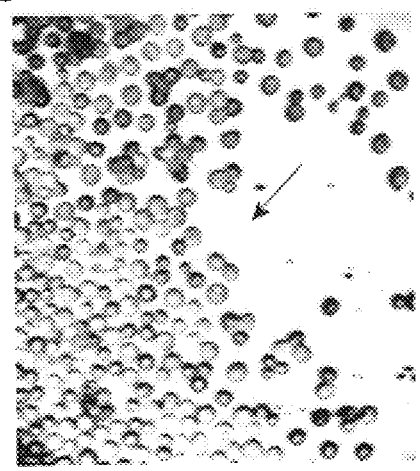
FIG. 13 is an illustration of the same effect as in FIG. 12, with S. cerevisiae cells (baker's yeast). (Bright field image. 25×obj, NA 0.45; electric field: 5V, 400 Hz)

Referring now to FIG. 13, therein is illustrated the same effect as in FIG. 12, with *S. cerevisiae* cells (baker's yeast). (Bright field image. 25×obj, NA 0.45; electric field: 5V, 400 Hz).

B. Cells Assemble in Accordance with Projected Illumination Patterns.

Figure 14:
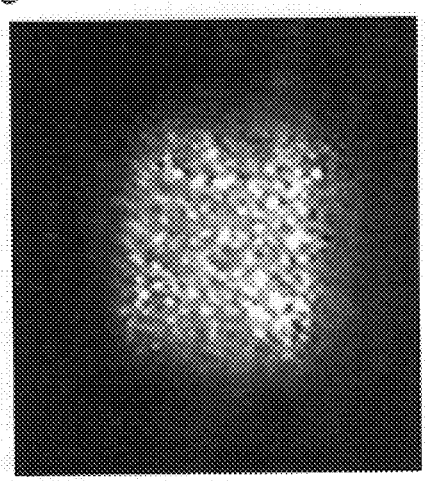
FIG. 14 is an illustration of E. coli forming diamond shapes that are projected to the surface by an LCD panel controlled by appropriate graphics software; (20×objective, NA 0.28; Electric field: 10V, 7 kHz)

Referring now to FIG. 14, therein is illustrated *E. coli* forming diamond shapes that are projected to the surface by an LCD panel controlled by appropriate graphics software; (20×objective, NA 0.28; Electric field: 10V, 7 kHz).

Figure 15:
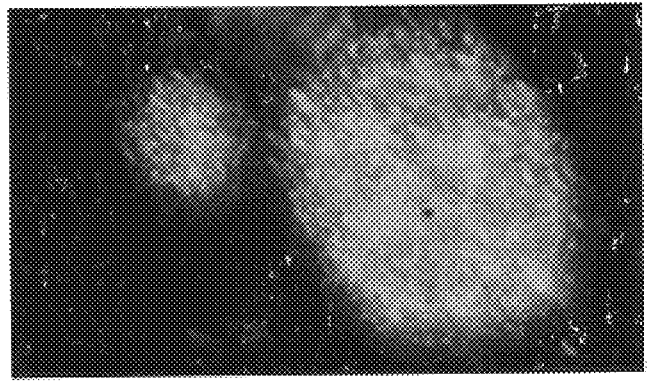
FIG. 15, is an illustration of S. cerevisiae responding to two circular illumination patterns;(20×objective, NA 0.28; Electric field: 15 V, 15 kHz)

Referring now to FIG. 15, therein is illustrated *S. cerevisiae* responding to two circular illumination patterns;(20× objective, NA 0.28; Electric field: 15 V, 15 kHz).

C. Light-directed Cell Transport and Reconfiguration of Cellular Assemblies

By enabling the controlled transport of cells and cellular assemblies in accordance with the PARSE format, the cytometry according to the present invention provides an entire additional level of cellular analysis which has the inherent capability to fractionate cell populations "in-situ".

The principal approach according to the present invention is to generate gradients in electrochemial properties of the interface to which sub-populations of cells exhibit a differential response. Such gradients may be produced by invoking patterns of illumination in geometry, as disclosed herein. Examples in the figures illustrate that cells respond to these patterns in a variety of ways.

Figure 16:
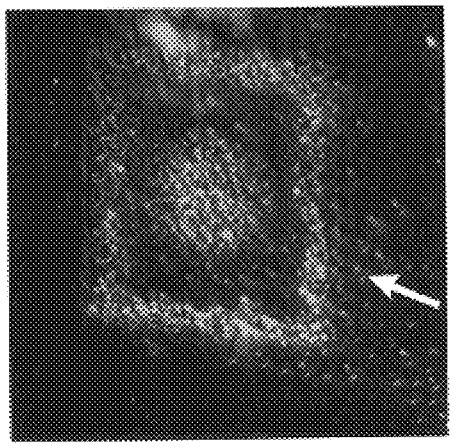
FIG. 16 is an illustration of S. cerevisiae responding to illumination, with an arrow indicate the direction cells are moving in or being expelled from the illuminated regions (20×objective, NA 0.28; Electric field: 15 V, 15 kHz)
Figure 17:
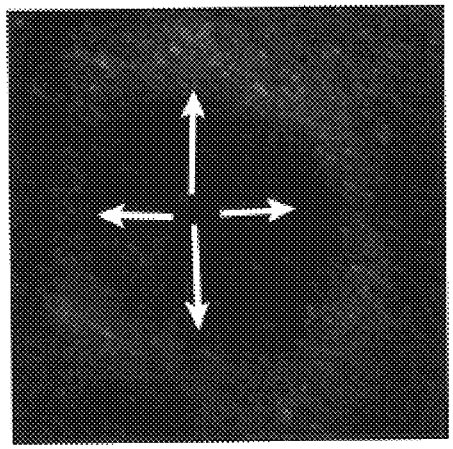
FIG. 17 is an illustration of E. Coli cells being repelled from the illumination circle(20×objective, NA 0.28; Electric field: 10 V, 7 kHz; low substrate doping level (1 Ohm cm–10 Ohm cm))
Figure 18:
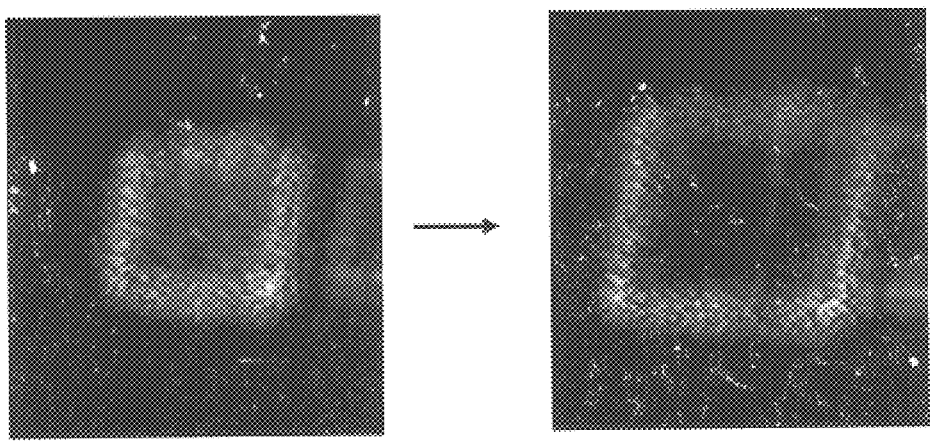
FIG. 18 is an illustration of E.coli cells following the expansion of the rectangular illuminated shape (20× objective, NA 0.28; Electric field: 15 V, 8 kHz)

For example, cells may be collected into illuminated regions (FIG. 16; *S. cerevisiae* responding to the illumination. Arrow indicate the direction cells are moving in. (20×objective, NA 0.28; Electric field: 15 V, 15 kHz)) or expelled from illuminated regions (FIG. 17; *E. Coli* cells being repelled from the illumination circle.(20×objective, NA 0.28; Electric field: 10 V, 7 kHz; low substrate doping level (1 Ohm cm–10 Ohm cm)); "channeled" by reconfiguring illuminated regions or "dragged" and "dropped" by displacing illuminated regions (FIG. 18; *E. coli* cells following the expansion of the rectangular illuminated shape (20×objective, NA 0.28; Electric field: 15 V, 8 kHz)).

Figure 19:
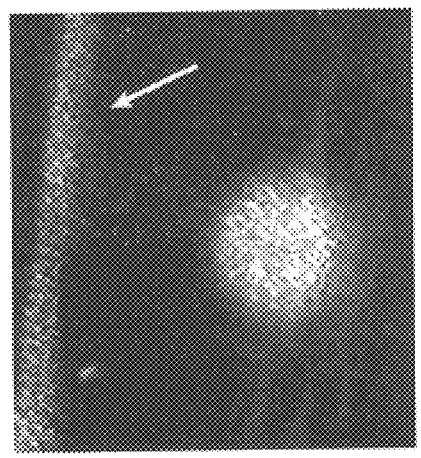
FIG. 19 is an illustration of E. coli cells being trapped by the light stripe at the left and being prevented from moving to the circular region on the right (20×objective, NA 0.28; Electric field: 15 V, 8 kHz)

Cells also may be "trapped" in well defined regions in response to light-induced spatial gradients in the electrical properties of the EIS structure (FIG. 19; *E. coli* cells being trapped by the light stripe at the left and being prevented from moving to the circular region on the right. (20× objective, NA 0.28; Electric field: 15 V, 8 kHz)). This set of fundamental operations permits the creation of spatially varying electrochemical potentials and corresponding lateral, highly inhomogeneous electric fields. In addition, the cytometry according to the present invention permits the programmable lateral displacement and reconfiguration of illumination patterns so that the location and the strength of the spatial inhomogeneities in electric fields can be adjusted at will.

Figure 20:
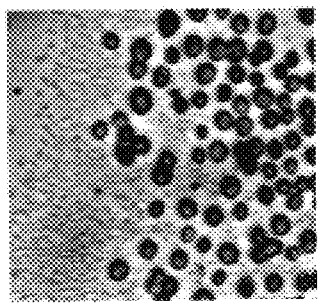
FIG. 20 is an illustration of an illuminated region containing both types of cells being suddenly expanded or "dragged", with E. coli cells (left) responding faster than the larger S. cerevisiae cells (right), resulting in segregation. (Bright field image. 25×obj, NA 0.45 Electric field: 5V, 400 Hz)

In addition, the cytometry according to the present invention also provides frequency-dependent forces to which different constituents within mixtures of cells will generally exhibit differential responses. An example of segregation between different types of cells is shown in FIG. 20 As shown in FIG. 20, when an illuminated region containing both types of cells is suddenly expanded or "dragged", *E. coli* cells (left) respond faster than the larger *S. cerevisiae* cells (right), resulting in segregation. (Bright field image. 25×obj, NA 0.45 Electric field: 5V, 400 Hz).

Specifically, on the basis of the known dielectrophoretic properties of various cells, fractionation will be possible on the basis of characteristic frequency dispersion . For example, the characteristic transition of cells from positive to negative dielectrophoresis (as evidenced in electrorotation; see e.g.: Huang et al, op. cit.) will be the basis for the fractionation of cell mixtures in light-induced gradients in electrochemical EIS potential (and the resulting inhomogeneous fields): different cells will be expelled from confined regions on the substrate at characteristic frequencies and light intensities.

D. Non-viable Cells Behave Differently than the Viable Cells.

The present inventors have observed that heat treated *S. cerevisiae* cells stop responding to the electric field and light after the first ten to twenty seconds and adhere to the substrate.

EXAMPLE

Immunophenotyping

Figure 21:
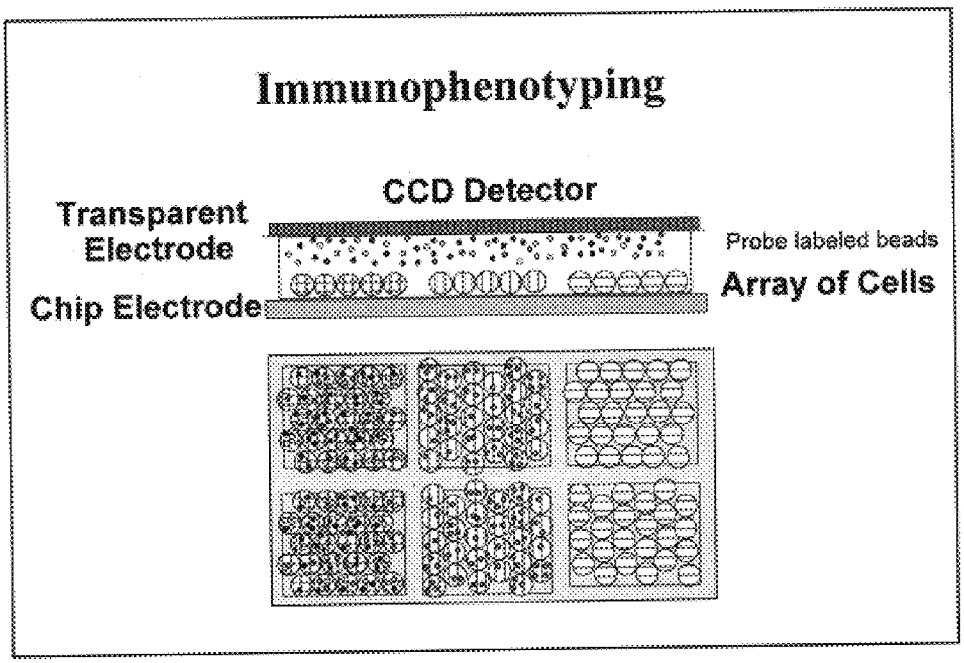
FIG. 21 is an illustration of immunophenotyping according to the present invention.

In a manner analogous to READ, a cellular array format will provide a sensitive and highly parallel mode of monitoring the presence of characteristic cell surface markers as illustrated in FIG. 21. For example, groups of lymphocyte cells can be put into array format on the substrate. Antibodies for the cell surface markers (CD3, CD4, CD8, CD56, etc.) are coupled to small microspheres that are differentially coded. The mixture of beads with different antibodies are directed to the cells arrays using the optical arrangement principles of the present invention. Antibodies on the bead surface will bind to the cell surface markers, thus, the correspondent beads will link to the cells. The number of surface markers which can be detected simultaneously depends on chemical coding capacity of the bead. Hundreds of chemical codings may possibly be used. Signal integration capability according to the present invention enables more accurate and quantitative analysis of the cells.

EXAMPLE

Multiplexed Affinity Detection

Figure 22:
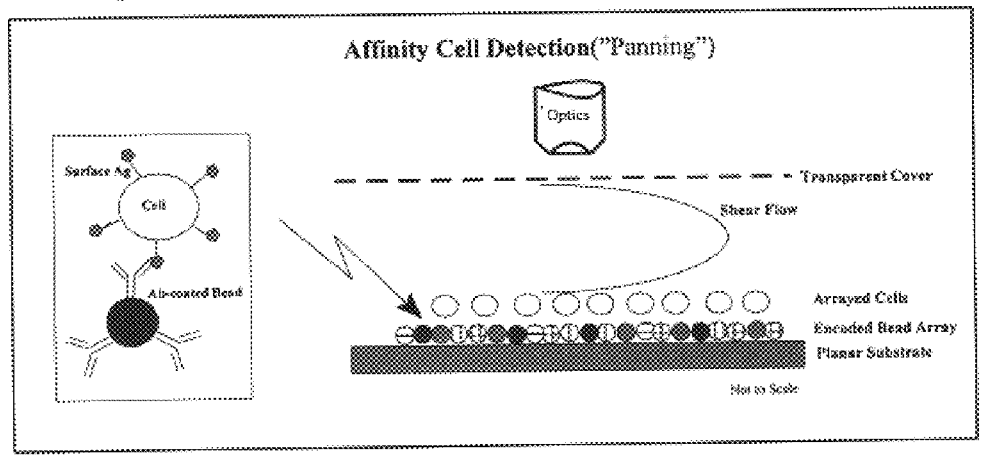
FIG. 22 is an illustration of affinity cell detection according to the present invention.

A novel format enabling the simultaneous affinity identification of multiple types of cells is shown in FIG. 22. A random encoded bead array of antibodies will provide a novel, highly diverse set of anchoring points for lymphocytes displaying cognate cell surface antigens. Under conditions of controlled stringency, flow-induced shear will remove cells that are not specifically bound while leaving "positives" attached to individual beads. Focusing on this downstream step takes advantage of the intrinsic "concentration" of sample on the cell surface and the ability to capture, with a single antibody probe, multiple pathogens sharing common processed antigenic determinants.

EXAMPLE

Light-guided Sorting and Isolation

Figure 23:
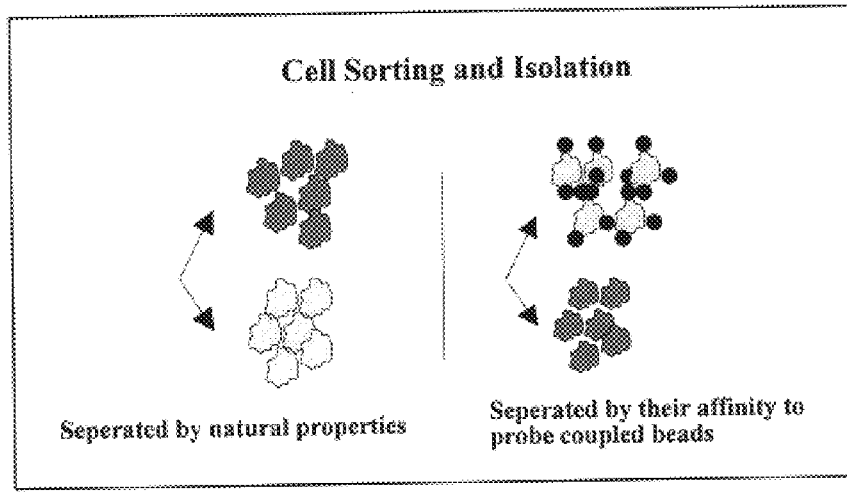
FIG. 23 is an illustration of cell sorting and isolation according to the present invention.

Combination of AC electric fields with light-controlled modulation of surface-electrochemical properties is particularly powerful. The illuminated areas mimics the behavior of patterned electrodes and can be repositioned in real time to isolate designated cells. Cells can be sorted and isolated due to their natural properties or due to the property change caused by specific binding to probe labeled beads. The model is illustrated in FIG. 23. Cells can be recovered after the isolation and further culturing or analysis may be performed. Specific lymphocyte cells and cancer cells may be of particular interest for such cell sorting and analysis.

EXAMPLE

Cell-based Functional Assays

Figure 24:
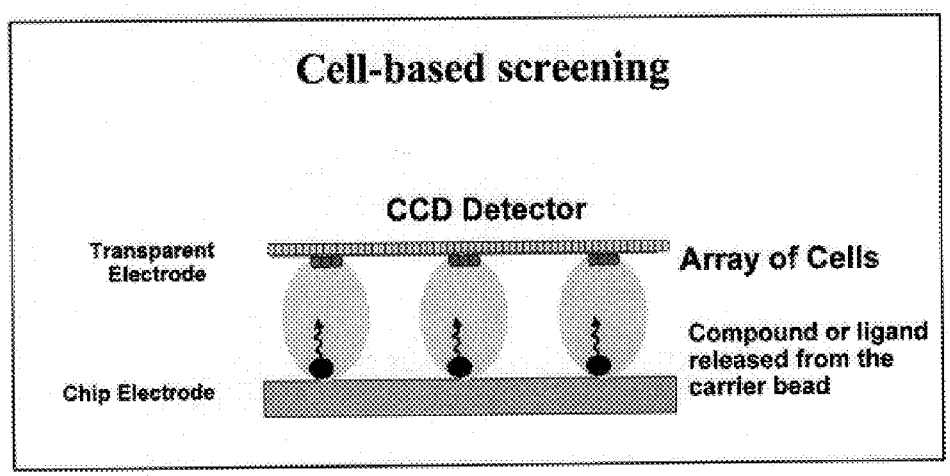
FIG. 24 is an illustration of cell-based screening according to the present invention.

Cell-based functional assays may be performed in a highly efficient manner by assembling cellular arrays and imaging reaction of the cells as shown in FIG. 24. The reaction may be the direct change of extracellular markers, or the endpoints of some metabolic pathways. The endpoints may be intracellular fluorescence signal generated by enzymes such as $\beta$-lactamase whose substrate can penetrate the cells, thus, the signal may be directly quantitatively detected by imaging (Zlokarnik et al., "Quantitation of Transcription and Clonal Selection of Single Living Cells with $\beta$-lactamase as Reporter", Science 279, 84–88 (1998); see also: Bronstein et al, "Chemiluminescent and Bioluminescent Reporter Gene Assays", Anal. Biochemistry 219, 169–181 (1994); the contents of all of which are incorporated herein by reference). If combined with microfludic control, such cell-based functional assays have tremendous applications in drug screening and ligand analysis. Cells may be placed at the same location as the chemical carrier beads. Under temporal and spacial controlled release of the compounds or ligands, response of the cells may be recorded. After image analysis, compounds or ligands that generate the desired cell response may be easily identified. Because the cells may be directly imaged, cell lysis and the following assays will generally not be necessary as part of the traditional cell-based analysis. Furthermore, the controlled assembly of the cells and chemical carrying beads, according to the present invention, may eliminate the use of microtiter plates in the cell-based screening.

EXAMPLE

Integrated Format Profiling of Secreted Cellular Markers

Figure 25:
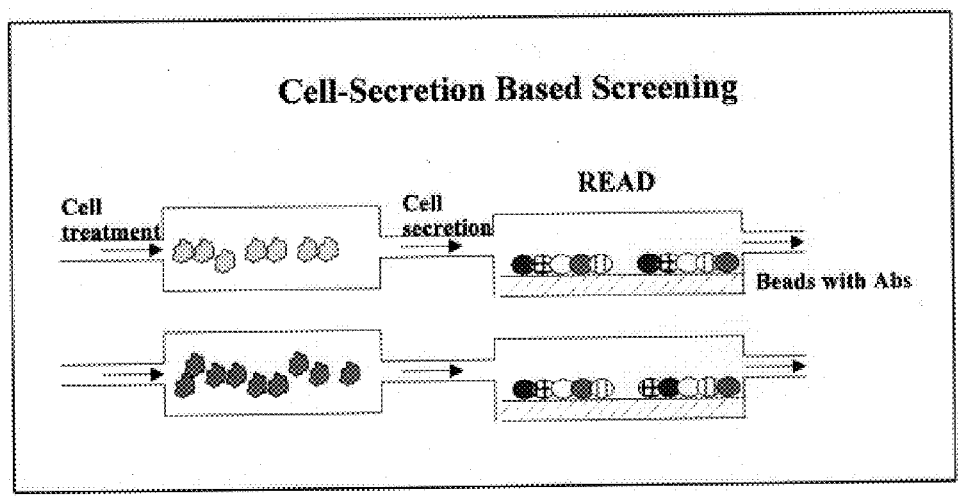
FIG. 25 is an illustration of cell-secretion based screening according to the present invention.

Control of cell assembly and microfluidic pathway enables direct in situ screening of secreted cellular markers. This model is illustrated in FIG. 25. Cellular arrays are assembled in one compartment of a two-compartment liquid reactor and are exposed to candidate drugs; the response is measured by monitoring a panel of secreted markers such as cytokines. Cell secretion are collected and introduced into a second compartment where they are profiled based on the response of a pre-deposited bead array using the READ format. Such a two-compartment reactor may be operated in parallel for multiple drug screening or kinetic analysis.

EXAMPLE

Cell-to-Cell Interaction

Figure 26:
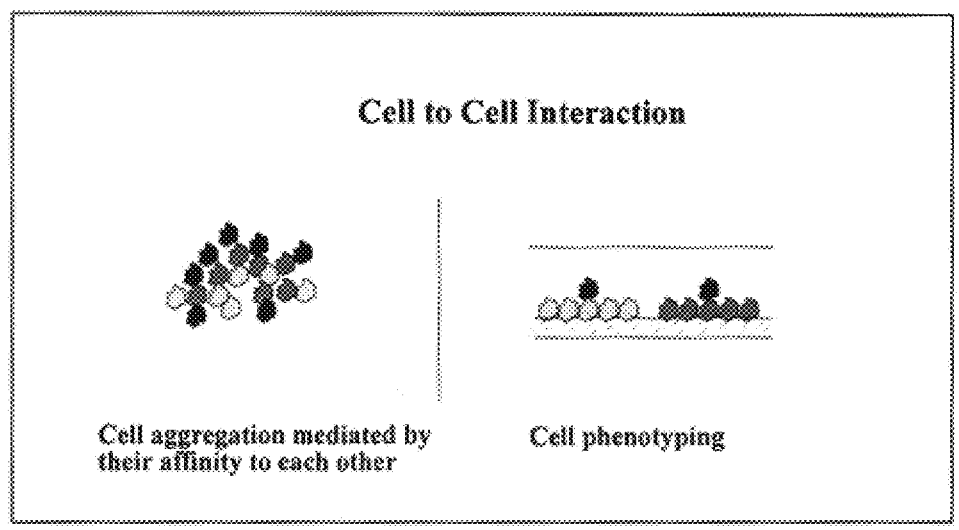
FIG. 26 is an illustration of cell to cell interaction according to the present invention.

Cell-to-cell in vivo interaction was seldom studied directly due to the lack of control in cell manipulation. The present invention provides a powerful tool in this area. As illustrated in FIG. 26, cells may be temporally and spatially controlled to favor the binding between the cells. Alternatively, cells may be directed to preassembled cell arrays for cell binding analysis. It may also be possible to study the interaction between cells such as T cells, B cells and polymorphonulear leukocytes, in the activation of immune responses.

EXAMPLE

Chemotaxis Analysis

Figure 27:
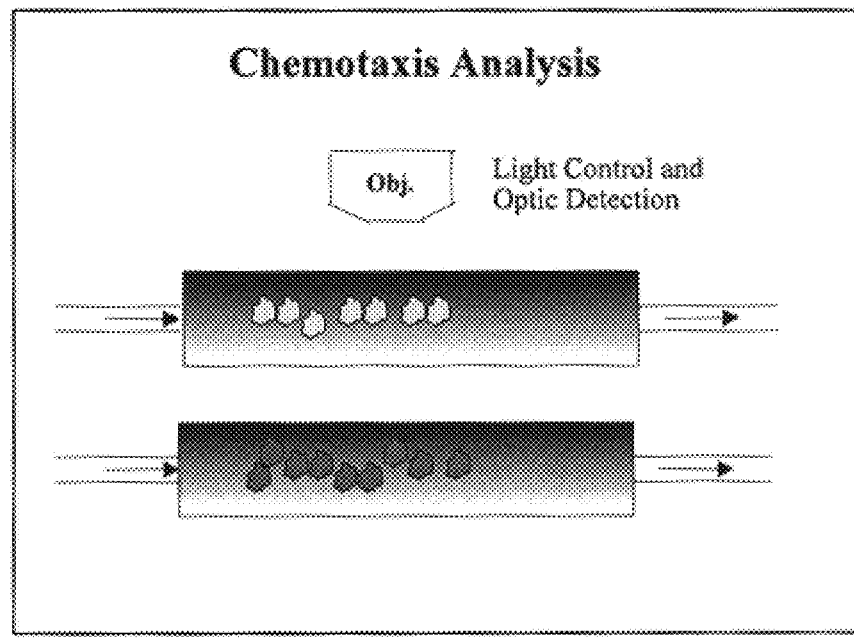
FIG. 27 is an illustration of chemotaxis analysis according to the present invention.

Cells can be positioned in a controlled configuration to test their chemotaxis properties. This model is illustrated in FIG. 27. For example, D. discoideum cells may be tested under cAMP or specific polypeptide gradient. (Parent & Devreotes, "A cell's sense of direction", Science 284, 765–770 (1999); the contents of which are incorporated herein by reference). Response of the receptors, G proteins, actin or actin-binding proteins may be detected through fluorescence signal generated by their correspondent fusion protein with GFP (Green Fluorescent Protein). Movement of the cells may also be recorded. More importantly, the force of the movement may be measured by comparing to the energy used in the light control of the cells.

The present invention may be used for cell identification and detection, for example, in immunophenotyping and affinity cell detection. In this application, affinity probes are coupled to beads on a solid surface. The beads are chemically and spatially coded. The cells are transported to the desired position using light control. Cells with the surface markers will bind at the correspondent positions. The advantages of this approach include a simpler and less expensive system, a higher degree of throughput for parallel immunophenotyping, the manipulation of a large number of cells, thus the detection of rare events, and better integration between the reaction and the detection steps, thus allowing the entire process to be performed on-chip.

The present invention may also be used in cell sorting, fractionation and isolation. In this case, cells can be separated according to their intrinsic properties, such as their dielectrophoretic mobility, viability, size, etc. Cells can also be sorted by their association with antibody coupled beads. The advantages of this approach include multiple cell sorting, simpler substrate fabrication, and flexible and programmable control.

The present invention may also be used for screening, for example, cell mediated drug and ligand screening, or cell secretion mediated screening. In this approach, cells may be transported and assembled a the desired position. Chemical compounds or ligands are released at the corresponding position. The response of the cells may then be observed through their reporter genes. The advantages of this approach include higher throughput, a simpler system without the complication of automated pipetting machines, and the possible combination with microscopy for simpler and more direct assays.

The present invention may also be used for cell to cell interaction, for example, in suspension or on surface interaction. In this approach, cells may link with each other through their surface interaction. Movement of the cells may then be guided by light. The advantages of this approach include the ability to study the interaction between cells.

While the invention has been particularly shown and described with reference to a preferred embodiment thereof, it will be understood by those skilled in the art that various changes in form and details may be made therein without departing from the spirit and scope of the invention.

What is claimed is:

1. A method of forming an assembly of cells in a designated area on a light-sensitive electrode, comprising:

providing a plurality of cells suspended at an interface between said light-sensitive electrode electrolyte solution;

generating an electric field at the interface; and illuminating the interface with a predetermined light pattern to form a planar assembly of substantially one layer of cells in a designated area on the light-sensitive electrode, wherein the designated area is defined by the pattern of illumination.

2. The method of claim 1, further comprising an additional electrode, the additional electrode and the light-sensitive electrode being substantially planar and aligned to one another and separated by a gap, wherein the additional electrode comprises an optically transparent electrode and wherein the gap contains the plurality of cells.

3. The method of claim 1, wherein the electrode has a surface or an interior, the surface or interior having been modified to produce spatial modulations in properties of the electrode, said properties affecting the local distribution of the electric field at said interface, wherein the surface or interior have been modified by spatially modulated oxide growth, surface chemical patterning or surface profiling.

4. The method of claim 1, further comprising the step of spatially or temporally varying the light pattern to cause the alteration of the assembly, said alteration being selected from the group consisting of disassembly, disassembly followed by reassembly, repositioning of the assembly, reconfiguration of the assembly, and segmentation of the assembly.

5. The method of claim 1, further comprising the step of varying the frequency or the voltage of the electric field to cause the alteration of the assembly, said alteration being selected from the group consisting of disassembly, disassembly followed by reassembly, repositioning of the assembly, reconfiguration of the assembly, and segmentation of the assembly.

6. The method of claim 1, in which the plurality of cells comprises more than one type of cells, the method further comprising the step of fractionating one type of cells from another to induce a displacement of the plurality of cells within the assembly, fractionation arising as a result of differences in mobility of said types of cells.

7. The method of claim 1, further comprising the step of maintaining the cells in the assembly, wherein the maintenance step comprises maintaining the electric field and the predetermined light pattern, or immobilizing the cells by chemical or physical means.

8. The method of claim 7, in which the cellular assembly is immobilized on the electrode by chemically linking the cells or confining the cells.

9. An assembly of cells formed in a designated area on a light-sensitive electrode, comprising the light-sensitive electrode; and a planar assembly of cells comprising substantially one layer of cells in said designated area on the light-sensitive electrode, wherein the assembly is formed according to the method of claim 1.

10. A method of conducting a bioassay involving an assembly of cells, comprising:

provining a planar assembly of cells comprising substantially one layer of cells in a designated area on the light-sensitive electrode and wherein the assembly of the cells is formed according to the method of claim 1;

contacting the cells with an analyte; and detecting the binding of the analyte to the cells.

11. The method of claim 10, in which the cells in the assembly of the cells are immobilized prior to contacting the cells with the analyte.

12. The method of claim 11, in which the cells are immobilized by chemically linking the cells or confining the cells.

13. The method of claim 10, in which the analyte is directed to a specific cellular marker, and the bioassay is for determining the presence of the cellular marker on the surface of the cells.

14. The method of claim 13, in which the bioassay is directed to cell typing, with the presence of the marker on the cell surface indicating the cell type.

15. The method of claim 13, wherein the analyte is attached to a label and the detection of the binding of the analyte to the cells is carried out by detecting the presence of the label.

16. The method of claim 13, further comprising the step of removing the analyte that is not bound to the cell before the detection step is carried out.

17. The method of claim 13, wherein the analyte is attached to a label, said label comprising a flourescent tag.

18. The method of claim 13, wherein the analyte is attached to a label, said label comprising a bead which is distinguishable by chemical or physical characteristics.

19. The method of claim 13, in which more than one analyte is tested simultaneously for binding with the cells, with each analyte being attached to an encoded bead that is distinguishable by chemical or physical characteristics, and the detecting step comprising decoding the beads bound to the cells to determine the respective identities of analytes bound to the cells.

20. The method of claim 13, wherein the analyte is a ligand directed to a specific cellular receptor and the bioassay is for determining the presence of the receptor on the surface of the cells.

21. The method of claim 13, wherein the analyte is an antibody directed to a specific cellular antigen, and the bioassay is for determining the presence of the antigen on the surface of the cells.

22. The method of claim 13, in which the presence of more than one antigen is determined using more than one antibody, wherein each antibody is attached to a fluorophore tag that is chemically distinguishable, wherein the detection step comprises multicolor imaging of the cells.

23. A method of assaying the binding of cells with a ligand or an antibody, said method involving a planar assembly of cells and comprising:

providing an assembly of cells prepared according to claim 1, wherein the assembly further comprises a plurality of beads randomly mixed with the cells in the designated area on the light-sensitive electrode, said beads having a ligand or antibody attached to their surfaces, wherein said beads comprise different types of beads distinguishable by the ligand or antibody attached thereto and further distinguishable by a unique chemical or physical characteristic that identifies said bead type;

allowing the binding interaction to occur between the cells and the ligand or antibody;

disassembling the mixed assembly of the cells and the beads; and detecting the binding interaction by analyzing the formation of clusters composed of the cells and the beads, the binding indicating the presence or absence of a cellular receptor or an antigen specific for the ligand or the antibody.

24. A method of determining a cellular response to an analyte, the method involving an assembly of cells and comprising: providing a planar assembly of cells formed according to claim 1; contacting the cells with an analyte; and detecting a cellular response to the analyte.

25. The method of claim 24, wherein th e analyte comprises a drug molecule or a ligand.

26. The method of claim 24, in which the cellular response being detected is an expression of a particular gene, said expression being determined by detecting for the presence of an intracellular reporter gene product.

27. The method of claim 26, in which the expression of the intracellular reporter gene yields intracellular fluorescence.

28. The method of claim 24, in which the cellular response being detected is selected from the group consisting of: morphological change of the cells, change in the cell membrane permeability, and a change in th e chemiotaxis response by monitoring the movement of cells.

29. A method of detecting a cellular response to an analyte, the method involving an assembly of cells and comprising: providing a planar assembly of cells prepared according to the method of claim 1; contacting the cells with an analyte; and detecting a cellular response to the analyte.

30. The method of claim 29, wherein one or more analytes are being tested for its ability to induce the cells to secrete one or more biologically active substances, and the detection step comprises detecting the presence of the biologically active substances.

31. The method of claim 30, wherein the biologically active substance comprises cytokine.

32. A method of determining a cellular response to an analyte, the method comprising:

providing a first electrode positioned in a first plane and a second electrode positioned in a second plane different from the first plane, the second electrode comprising a light-sensitive electrode and the first and the second electrode each comprising a planar electrode and said electrodes being in a substantially parallel alignment and separated by a gap, said gap containing an electrolyte solution in which a plurality of cells is suspended;

providing a planar array of beads on the first electrode, said beads having a ligand attached to their surfaces in a releasable manner, wherein said beads comprise different types of beads distinguishable by the ligand attached thereto and further distinguishable by a unique chemical or physical characteristic that identifies said bead type illuminating an interface between the light-sensitive electrode and an electrolyte solution with a predetermined light pattern and generating an electric field at said interface to form a planar assembly of the cells on the second electrode, with the gap area separating the beads from the assembled cells; and releasing the ligand and monitoring a cellular response, the proximity of the cells to the bead array permitting determination of the identity of the ligand inducing the cellular response.

* * * * *

UNITED STATES PATENT AND TRADEMARK OFFICE
CERTIFICATE OF CORRECTION

PATENT NO. : 6,387,707 B1 Page 1 of 1
APPLICATION NO. : 09/320274
DATED : May 14, 2002
INVENTOR(S) : Michael Seul and Alice Xiang Li It is certified that error appears in the above-identified patent and that said Letters Patent is hereby corrected as shown below:

Claim 1, column 42, line 12, after the word "electrode" and before "electrolyte", insert --and an--.

Signed and Sealed this

Sixteenth Day of September, 2008

JON W. DUDAS
*Director of the United States Patent and Trademark Office*